United States Patent [19]

Berka et al.

[11] Patent Number: 5,360,732

[45] Date of Patent: Nov. 1, 1994

[54] PRODUCTION OF *ASPERGILLUS NIGER* CATALASE-R

[75] Inventors: Randy M. Berka, San Mateo; Timothy Fowler, Redwood City; Michael W. Rey, San Mateo, all of Calif.

[73] Assignee: Genecor International, Inc., Rochester, N.Y.

[21] Appl. No.: 846,181

[22] Filed: Mar. 4, 1992

[51] Int. Cl.$^5$ .................. C12N 15/53; C12N 15/80; C12N 1/21; C12N 9/08

[52] U.S. Cl. .................. 435/192; 435/69.1; 435/71.1; 435/254.3; 435/320.1; 435/172.3; 536/23.2; 935/14; 935/27; 935/36; 935/56; 935/68

[58] Field of Search .............. 435/69.1, 71.1, 192, 435/254, 320.1, 172.3, 254.3; 536/27, 23.2; 935/14, 27, 36, 56, 68

[56] References Cited

PUBLICATIONS

Belyavsky, A. et al. "PCR-Based cDNA Library Construction: . . . " Nuc. Acids. Res. 17(8) 2919-2932 (Apr. 1989).
Berger, S. L. et al. (eds.) "Guide to Molecular Cloning Techniques." Meth. in Enzymol. vol. 152, pp. 393-399, 415-423, 432-447, 661-704 (1987).
Deutscher, M. P. (ed.) "Guide to Protein Purification" Meth. in Enzymol. vol. 182, pp. 602-613, 738-751 (1990).
Gruft, et al., 1978, Can. J. Biochem., 56:916-919.
Mosavi-Movahedi, et al., 1987, Int. J. Macromol. 9:327-332.
Kikuchi-Torii, et al., J. Biochem. 92:1449-1456.
Cullen, et al., 1987, Bio/Technology 5:369-376.
Barton, et al., 1972, J. Bacteriol. 111:771-777.
Fowler, et al., 1990, Current Genetics 18:537-545.
Van Hartingsveldt, et al., 1987, Mol. Gen. Genet. 207:71-75.
Wilson, et al., 1988, Nucl. Acids Research 16:2339.

*Primary Examiner*—Robert A. Wax
*Assistant Examiner*—Rebecca Prouty
*Attorney, Agent, or Firm*—Karen I. Krupen

[57] ABSTRACT

The invention discloses the application of genetic engineering techniques to create novel strains of *A. niger* which produce high levels of catalase (catR gene product, catalase-R) while generating minimal sodium gluconate waste material.

9 Claims, 26 Drawing Sheets

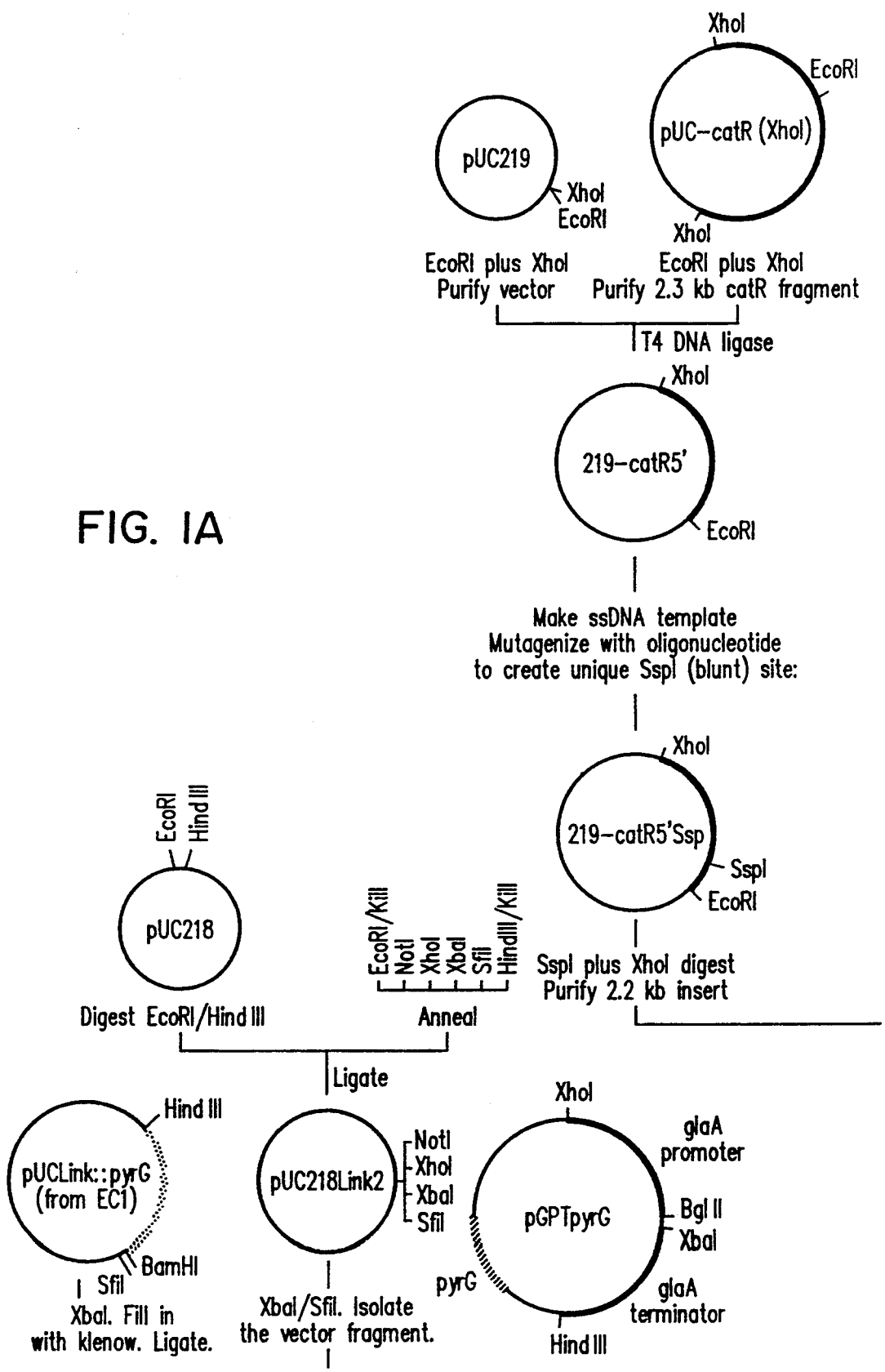
FIG. IA

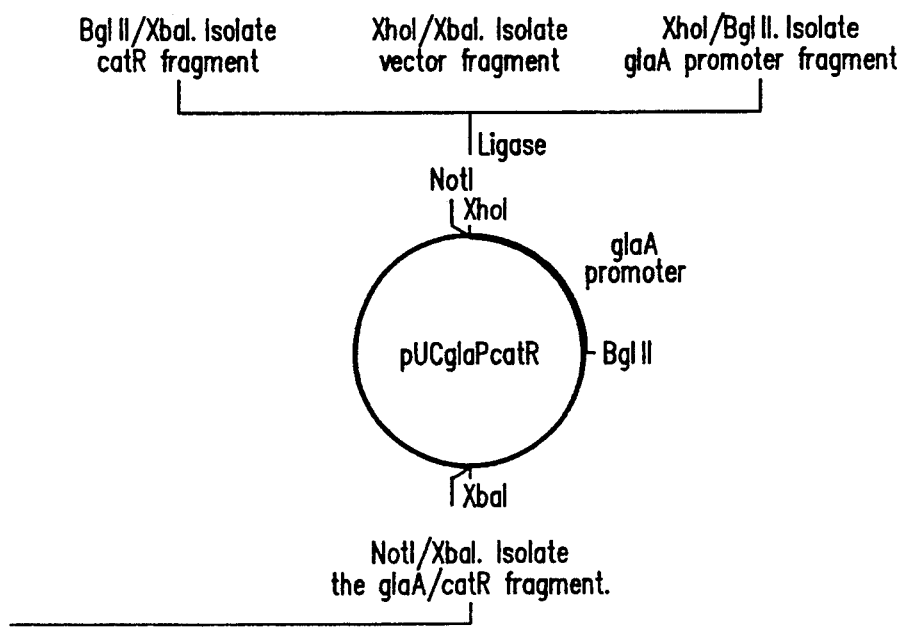
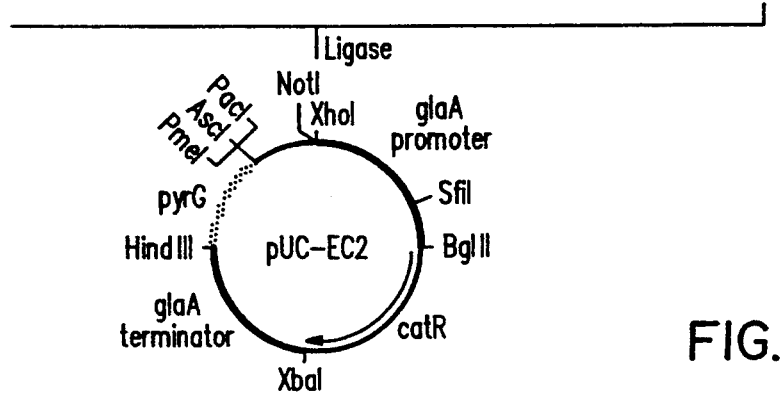
FIG. ID

```
                                                                                            Dra III
                                                                                              ...          Esp3 I        Bcl I
                                                                                                             ...          ...
CTTGTCACCGAGTGCCGTTTGTCACTTGTTGTGGTGATCTTGAGCACACATGCGTTCCTCTGTCTCATCACATGAGTGATCAACATTG        90
                        Esp3 I       Acc III
                          ...         ...
CATGACCCCTAGTGGAGCCCCTTCGTCTCCCAACAGGAGGGTCCGGATTACCAAGTCCCGACACCGTTTGGCTGTGTAATTCGACTCAAATTC   180
                Mlu I
                ......
             Eam1105 I .Hpa I                      .Nco I                  .Bln I
                ...     ...                         ...                     ...
TGGATTCGTAGCTTAACTAAGACGCGTGGTCTGTTAACCGGCCTCGCCATGGATGCCGATATAAGGACCCTAGGGACTCCCCCCTGTG        270
                                                                                              .Pvu II
                                                                                               ...
      .PshA I     .Bbv II
       ...         ...
ACTCTCGTCGGAAGATCGCAGCACTCTGAATTCTCCTAGTCTTCGTTACTCCGCCATGGTCATTTCTGCCTTTGCCAGCTGTTGCTG          360
                                                                Met Arg His Phe Trp Leu Leu Pro Ala Val Ala
                                                                                  .Taq II-2
                                                                                   ...
                                                                                .Age I
                                                                                 ...
GTATCGCTGGGGCTCAATGCCCCTACCTGTCGGGTGAAATGAGTTTCACCCAGGAGCAGGACAATGCTGGCGATACCATTGAGGTCACGG       450
Gly Ile Ala Gly Ala Gln Cys Pro Tyr Leu Ser Gly Met Ser Phe Thr Gln Glu Gln Asp Asn Ala Gly Asp Thr Ile Glu Val Thr

AGCAGCCCATTGACAACACCCTGTATGTCAATGACACCGGTAGCTACATGACTACGGACTTTGGCACTCCGATCTCCGACCAGACCAGTC      540
Glu Gln Pro Ile Asp Asn Thr Leu Tyr Val Asn Asp Thr Gly Ser Tyr Met Thr Thr Asp Phe Gly Thr Pro Ile Ser Asp Gln Thr Ser
    .Bsp120 I               .EcoN I       .Eco57 I       .HinDIII
     ......                  ...           ...           ...
     .Apa I
      ...
TCAAGGCCGGGCCCCCGTGGTCTCCACCCTGTTGGAGGACTTTATCTCCGTCAGAAGCTTCAGCGGTTCGACCATGAGCGTGTAAGTACAG    630
Leu Lys Ala Gly Pro Arg Gly Pro Thr Leu Leu Glu Asp Phe Ile Phe Arg Gln Lys Leu Gln Arg Phe Asp His Glu Arg - - - - -
```

| FIG. 2A-1 |
| FIG. 2A-2 |

```
.AlwnI
TAACTGCTGCGGTGTAGTAACAATAAATTGACCCAGTGGTTTTCAATTAGGTCCCCGAGCGCGTCGTCCAGCCCGTGGTGCCGGTGC    720
                                                              .BstXI
                             ------Val Pro Glu Arg Val Val His Ala Arg Gly Ala Gly Ala
.NdeI                                          .BsaI
ATATGGTACTTCAAATCCTACGCCGACTGGTCGAACGTCACGGGCTGCCGATTTCTTGAGTGCCAACGATAAGGAGAGCCCTATGTTCTG    810
Tyr Gly Thr Phe Lys Ile Ser Tyr Ala Asp Trp Ser Asn Val Thr Ala Ala Asp Phe Leu Ser Ala Asn Asp Lys Glu Pro Met Phe Cys
TCGCCTCTACTGTGGTCGGTTCCGTGGTAGTGTTGACACTGTTGACACGCTTGCGGTTCTCACACTGACGAGGG    900
Arg Phe Ser Thr Val Val Gly Phe Arg Gly Ser Val AspThr Ala Arg Asp Val His Gly His Ala Cys Arg Phe Tyr Asp Glu Gly
          .BstEII              .TaqII-2   .Tth111I
TAACTATGGTATCTTGATATGGTCACCCAACATAATTCAATACATGTCTAACAGATATGTCTCTACTAGACATCGTCGGTATCAATTTCG    990
Asn Tyr -------                             --- Asp Ile Val Gly Ile Asn Phe
                                                               .BsgI
CCCCCCTTCTTCATCAGGACGCCATCAGTTCCCGATCTGTCCAGGCCATCAAGCCCATGCCCAACAATGAGATCCCAGGCCGCTA    1080
Ala Pro Phe Phe Ile Gln Asp Ala Ile Gln Phe Pro Asp Leu Val His Ala Ile Lys Pro Met Pro Asn Asn Glu Ile Pro Gln Ala Ala
.Eco57I
CTGCACACACTTCCGCTTGGGACTTCTTCAGCCAGCAGAGAGGCCACTGCCCTCCACAGTGCCTTGTGCCTGATGTCTGTAACGGTATTCCTC    1170
Thr Ala His Thr Ser Ala Trp Asp Phe Phe Ser Gln Gln Ser Thr Ala Leu His Ser Ala Leu Trp LeuMet Ser Gly AsnGly Ile Pro
                                                          |——— Peptide 1 ———
GTTCTTCCCGGCCACATGAACGGCTACGGAGTCCACAGCTTCCGCTTCCGCTTCGTGCTGCCAATGCACTTCCAAGGTGGTGCGAACACCTTGGA    1260
Arg SerPhe Arg His Met Asn Gly Tyr Gly Val His Ser Phe Arg Phe Val Ala Ala Asn Gly Thr Ser Lys Val Val Arg Thr Pro Trp
|——— Peptide 1 ———|           |——————— Peptide 5 ———————|
```

```
                     .RleA I         .Bpu10 I                                                  .Alwn I
              AGTCCAACAGGGTGTTGCCAGTCTGGTGTGGGATGAAGCTCAGGCCCGCTGGTAAGAACAGTGACTACCACCCCCAGGATCTGTACA  1350
              Lys Ser Gln Gln Gly Val Ala Ser Leu Val Trp Asp Glu Ala Gln Ala Ala Gly Lys Asn Ser Asp Tyr His Arg Gln Asp Leu Tyr
                                                              .BsaB I
                 .Bal I                                         .Cla I
              ATGGATGCCAATGGCCCACTACCCGAAATACGAGGTCAGGCCAATCCCTTGATGTCTATGATAGAGCCTTTTGCTGACAATCCCCTAGG  1440
              Asn Ala Met Pro Asn Gly His Tyr Pro Lys Tyr Glu - - - - - - - - - - - - - - - - - - - - - - - - - -
                 .PflM I
                                                .BamH I
                                                .Bsu90 I         .BstX I
              TCCAAGCCCAGATCATGATGAGGCTGACATGCTTCGTTTCGGCTTCGACCTTGGATCCAACAAGTTGGTCCCGAGGAGGTTGTCC  1530
              Leu Gln Ala Gln Ile Met Asp Glu Ala Asp Met Leu Arg Phe Gly Phe Asp Leu Leu Asp Pro Thr Lys Leu Val Pro Glu Val Val
                     .Ecl136 II
                     .Sac I                                                                   .Eco57 I
              CTTACACTCTCTCGAATGATGAGCTCAATGCCAACCCCACCAACTACTTTGCTGAAGTGAACAGGCTGGTGTATGTATTCCCCATT - -  1620
              Pro Tyr Thr Pro Leu Gly Met Met Glu Leu Asn Ala Asn Pro Thr Asn Tyr Phe Ala Glu Val Asn Arg Leu Val Tyr Val Phe Pro Ile
                                                                  .Pst I
              CATCAAATGCCAGATGAGACATAATCTAACTTCTGCAGTTCCAACCCGTCACGTCGTTCTGCATTGACTTCACGGACGACCCCTGTGCAA  1710
              - - - - - - - - - - - - - - - - - - - - - - - - Phe Gln Pro Gly His Val Val Pro Gly Ile Asp Phe Thr Asp Asp Pro Leu Gln
                .Esp3 I
                .Eam1104 I
              GGCCGTCTCTTCCTACCTCGACACTCAGTGACCCGTCCAACTTCGAGCAAATCCCCGTCAACCGTCTCGCAAGCCC  1800
              Gly Arg Leu Phe Ser Tyr Leu Asp Thr Gln Leu Thr Arg His Gly Gly Pro Asn Phe Glu Gln Ile Pro Val Asn Arg Pro Arg Lys Pro
                                                                                                    .BstE II
              GTTCACAACAACAACCGTGACGGCTTCGGCCAGCAGCAGATCCCCACCAACAACTGGGCCTACACCCCCAACAACAGGATGAGCAACGGTTAC  1890
              Val His Asn Asn Asn Arg Asp Gly Phe Gly Gln Gln Gln Ile Pro Thr Asn Asn Trp Ala Tyr Thr Pro Asn Asn Ser Met Ser Asn Gly Tyr
```

FIG. 2B-2

```
      Eam1105 I
         ..BstX I
         :::
CCCATGCAAGCCAACCAGACCAGGGTCATGGTTTCTTCACCGGCCTACCGCTTCCGGCCAGACCAGCCCG  1980
Pro Met Gln Ala Asn Gln Thr Gln Gly His Gly Phe Phe Thr Ala Pro Tyr Arg Tyr Ala Ser Gly His Leu Val Arg Gln Thr Ser Pro
                                                    ————— Peptide 4 —————
                                                    ▮▮▮▮▮▮▮▮▮▮▮▮▮▮▮▮▮▮▮▮

Eam1105 I                    PflM I
         :::                      :::
                                                           Esp I
                                                            :::
ACCTTCAATGACCACCTGGTCCCAGCCCGCCATGTTCTGGAACTCTCTGATCCCCGCTGAGCAGCAGATGGTTGTCAACGCCATTGTCTTT  2070
Thr Phe Asn Asp His Trp Ser Gln Pro Ala Met Phe Trp Asn Ser Leu Ile Pro Ala Glu Gln Gln Met Val Val Asn Ala Ile Val Phe
                                                                      ————— Peptide 3 —————
                                                                      ▮▮▮▮▮▮▮▮▮▮▮▮▮▮▮▮▮▮▮▮

Hpa I                                                                     Pvu II
     :::                                                                       :::
                                                                                                    Bsi I
                                                                                                     :::
GAGAACTCAAGGTTAACAGCCCCCACGTTCGGAAGAACGTTGTCAACATGGTCAACCAGCTGAACATGGTCAACAACAACCTCGCCGTCGCT  2160
Glu Asn Ser Lys Val Asn Ser Pro His Val Arg Lys Asn Val Val Asn Gln Leu Asn Met Val Asn Asn Asn Leu Ala Val Ala
     ————— Peptide 2 —————                                                                     ————— Peptide 2 —————
     ▮▮▮▮▮▮▮▮▮▮▮▮▮▮▮▮▮▮▮▮                                                                     ▮▮▮▮▮▮▮▮▮▮▮▮▮▮▮▮▮▮▮▮

Bsa I                                                  Acc65 I
     :::                                                    ..Kpn I
                                                            :::
CGTGGTCTTGGTCTCGATGAGCCCTCCCCCAACCGGAGACTTACTACACCTCCAACAAGACCTCCAACGTCGGTACCTTCGGGCAAGCCCCTC  2250
Arg Gly Leu Gly Leu Asp Glu Pro Ser Pro Asn Pro Thr Tyr Tyr Thr Ser Asn Lys Thr Ser Asn Val Gly Thr Phe Gly Lys Pro Leu
```

FIG. 2B

| FIG. 2B-1 | FIG. 2B-2 |

FIG. 2B

```
                                                                                      Nco I
Bpu10 I   BspM I    Pst I                                                            ;Pfl M I
  ;...    ;...   ;...                                                                ;...;..
CTCAGCATCGAGGGTCTGCAGGTCGGCTTCCTGGCCTTCTGCTTGAACTCCCACCCCGAATCCATCAAGCAGGGCCAGGCCATGGCCGGCCAGTTC  2340
Leu Ser Ile Glu Gly Leu Gln Val Gly Phe Leu Ala Ser Asn Ser His Pro Glu Ser Ile Lys Gln Gly Gln Ala Met Ala Ala Gln Phe
                          ;Sal I                        ;Stu I
                          ;...                          ;...
TCTGCCGCTGGCGTCGACCTGAACATTGTCACCGAGGCCTACGCCGATGTGTCAACACCACCTACGCCCTGTCTGATGCCATCGACTTT  2430
Ser Ala Ala Gly Val Asp Leu Asn Ile Val Thr Glu Ala Tyr Ala Asp Val Asn Thr Thr Tyr Ala Leu Ser Asp Ala Ile Asp Phe
                                                .Eam1104 I
                                                ;.Bsg I
                                                ;......
GACGCCCTCATCATCGCCGATGGTGTGCAGAGCCTCTTCGCCCTCTCGCTAACCAGATGAACTCTACGCCACCTCTACTCTC  2520
Asp Ala Leu Ile Ile Ala Asp Gly Val Gln Ser Leu Phe Ala Ser Pro Ala Leu Ala Asn Gln Met Asn Ser Thr Ala Thr Ser Thr Leu
         ;Alwn I
         ;Pfl M I
         ;...
TACCCTCCTGCCAGACCTTTCCAGATCCTGGTCGATTCTTTCAGGTACGGTAAGCCCGTGTCTCGGGCAGTGGCAGTGTTGCCGCTC  2610
Tyr Pro Pro Ala Arg Pro Phe Gln Ile Leu Val Asp Ser Phe Arg Tyr Gly Lys Pro Val Ala Ala Val Gly Ser Gly Ser Val Ala Leu
                  ;Xho I
                  ;Esp3 I
                  ;Mla AI
                  ;Sci I
                  ;...
AAGAACGCTGGTATTGATTCCTCCCGCTCTGGTGTGTACACTGGCTCGAGCGAGACGACCGAGAAGATCGCCAAGGAGGTCTTGGAGGGA  2700
Lys Asn Ala Gly Ile Asp Ser Ser Arg Ser Gly Val Tyr Thr Gly Ser Ser Glu Thr Thr Glu Lys Ile Ala Lys Glu Val Leu Glu Gly
```

FIG.2C-1

```
                                                                              Age I
                                                                              :::
CTCTACACTTTCCGTTTGTGGACCGGTTTGCGCTGGATGAGTAAGGTATCACGTTTGTACTGTACTCACGTTCATCGTTTGTGATGA   2790
Leu Tyr Thr Phe Arg Phe Val Asp Arg Phe Ala Leu Asp Glu
                           Cla I                       Bst1107 I
                           :::                         :::
TACATTGATGATCGATAGATATTTTGTGAGATAGATAGAGTATACTAGAGWKACATATCTCTACTGATGAGGTGTTGTGCTGCTGCAA   2880
                  Eam1104 I,Nhe I                              Hpa I      Eam1104 I        BsaB I
                  :::                                          :::        :::              :::
CACATATTTATGAATATATATTCTCTCTTTGTGAAAGCTAGCCTTCTATATAATCAGCAATGGTTAACTCTTCCAATTCTATAGATACC   2970
AATCACCTAACCCACTCGGAATGACGACAGAAAAACATCGACATGTTCGCCCAAGTAAAGCTACTGAACTTCTACATTTATGCTATGCTG   3060
          Gsu I
          :::
GAGTCCTCTCATAAGTCCAGAATAAACAAAGAGATCCGATCCTGCTC   3107
```

FIG. 2C-2

| FIG. 2C-1 |
|-----------|
| FIG. 2C-2 |

FIG. 2C

```
GCGGCCGCCTCGAGGATTGTCTGAACATTGACATTCGGCGCCCAGCGAACCCCAACTGGGACGGACGCGAATGCCCGTGCTGGTCTCGGATCT       90
└linker┘                                    ─────────────── glaA promoter ───────────────

TTGGCGGAGCCTTTGAACTTGGTCAAAGGCCATGTGTTCAAAGGGCCATGTATGACGGCACAACGATGTATCATCGTCGATAGACAAGAATATGCCTATCGTGT       180
─────────────── glaA promoter ───────────────

TGTAGGCGATGAACTATCGCGTAGGGGCCTTCGGGTTTCTGCCCGGAAAGGAGATTCTGGAGGACGGGTCCGCCAACTTAGGTCTTTGAC       270
─────────────── glaA promoter ───────────────

CAAGCCCTTGCCCTAGTGGGTGTGCCGACAACATCGAGGCGTTTGGTGGAGACCAGACAAGGTGACAATCTCGGGAGAATCAGCAGGGGCTA       360
─────────────── glaA promoter ───────────────

TTTCTGTCTTGATCAGATGATCTGTACGACGGAAACATCGCTTACAAGGACACAAGCCCTTGTTCGGGAGCCATCATGACTCCGGGTATGT       450
─────────────── glaA promoter ───────────────

GTTCCCGCAGACCCTGTCGACGGGTCAAGGGATCAGCAAGTATATGCGGTTGTGGACTCTGCAGGCTGTGTTCCTCTTCCAACGACAC       540
─────────────── glaA promoter ───────────────

CCTGCCTTGTCTGCGTGAGCTAGACTACACCGACTATCTCAATCGGGCAAACTCGTGCCGGGATCCTAGGTTATCACCGTGGCGCTATC       630
─────────────── glaA promoter ───────────────

ATATGTGCCTCGACCAGACGGGACGGGCATTTGTCGCGTGCCCAGAGATTTTGGGTAAAGCAGGGAAGTATGCGCGGGTCCATTCATCGTG       720
─────────────── glaA promoter ───────────────

GGCGACCAAGAGGATGAGGGGACCTTGTTCGCCCTGTTCTTCAGTCCTTACGACGATCGCGACGAGTAGTCGACTATCTGGGCACTACTTCT       810
─────────────── glaA promoter ───────────────
```

FIG. 3A-1

TCTATGACGCTAGCCAGGAGCAGCTTGAAGAATTAGTGGCCCTGTACCCAGACACCACCACATATGGGCTCTCCCTTCAGGACGGGCAGGC      900
                                                                                             ——— glaA promoter ———

CAACAACTGTATCCGCAATTAAGCGATTGGCCCGCCAATTCTCGGCGACTTGGTCTTCACCATTACCCGGGCATTCCTGTCATATGCA      990
                                                                                             ——— glaA promoter ———

GAGGAGCTCTCCCCTGACCTCCCGAAATGGTCGTACCCTGGGCGACCTATGACTATGGCAGCCAATTCTCGGGACCTTCATGAAGTGACC      1080
                                                                                             ——— glaA promoter ———

TGCTGCAGGTGTTCTATGGGATCAAGCCGAACTATGCAGCCGAGTTCCAGCCACACGTATTATCTGAGTTTTGTATACACGCTGGATCCGA      1170
                                                                                             ——— glaA promoter ———

ACTCCAATCGGGGACATATGAGTTCATCCTGCAGAATACCGGCGAGTACATGAATGCCCCAGTGCAGCCGACAGTTGATGAATTTCGGAGCGAACAGTCTCCTTACGGATGAT      1260
                                                                                             ——— glaA promoter ———

TCCGCAACGGGACATATGAGTTCATCCTGCAGAATACCGGCGCGTTCCACATCTGATGCCATTCGGGAGGGTCCGAGGTCAGGGACT      1350
                                                                                             ——— glaA promoter ———

AGCCTTATGACGTAACGTAATGATGAAGTGCTGCGCCTCGGCCAAAGGATATATAGGGTCATAATAAGTAGTACTAGTTATATTAATGGAAGGG      1440
                                                                                             ——— glaA promoter ———

TATATACCACGCGTTGGACCTTGGGACCTGCATTATAGCTTCCCGTTAGGTATAATTACCGTTGTTATAGCAGCCAATCAGCCACCACG      1530
                                                                                             ——— glaA promoter ———

CTCGACCGGGGGGACGGGCGAATCCCCGGGAATTGCAATTGAAATAAATTCAGGTCAATGCGGGCCAGGACATTGGACACATCTCCAAGGCACA      1620
                                                                                             ——— glaA promoter ———

FIG. 3A-2

| FIG. 3A-1 |
| FIG. 3A-2 |

FIG. 3A

```
GGGCCATTCTGCAGTGCCGGGGATTCAGTGCATTCCCCCGGGCCCCGACACGCGATAGGCTGGTTCTTCCACACCACCGGAGATTC    1710
                                ——— glaA promoter ———

GTCGTTCTGAAGAGCTGAAGTGCCGAGATGGTCTCTGCAGGAATTCAAGCTAGATGCTAAGCGATATTGCATGGCAATATGTGTTGATGC    1800
                                ——— glaA promoter ———

ATGTGCTTCTTCCCTCCCCTCGTGCAGATGAAGGTTTGGCTATAAATTGAAGTGGTTGGTCGTCGGGGGTTCCGTGAGGGGCTGAAG    1890
                                ——— glaA promoter ———

TGCTTCCTCCCTTTTAGACGCAACTGAGAGCCTGAGCTTCATCCCCAGCATCATTAGATCTCAGCAATGGCTCATTTCTGGCTTTTGCTG    1980
                                ——— glaA promoter ———                    ——— catR coding region ———

CTGTTGCTCGATCGCGTGGCTCAATGCCCCTACTGTGTCGGGTGAAATGAGTTTCACCCAGGAGCAGGACAATGCTGGCGATACCATTGAGG    2070
——— glaA promoter ———                    ——— catR coding region ———

TCACGGAGCAGCCCATTGACAACACCCTGTATGTCAATGACACCGGTAGCTACTACATGACTACTCCGATCTCCGACCAGA    2160
                                ——— catR coding region ———

CCAGTCTCAAGGCCCGGGCCCGTGCTCCTACCCTGTTGGAGGACTTTATCTCCGTCAGAAGCTTCAGGGGTTCGACCATGAGCGGTAA    2250
                                ——— catR coding region ———

GTACAGTAACTGCTGCGGTGTGTAGTAACAATAAATTGACCCAGTGGTTTTCAATTAGGTCCCGAGCCGCTGTCGTCCACGCCCGTGGTGC    2340
                                ——— catR coding region ———

CGGTGCATATGGTACTTTCAAATCCTACGCGCTGGTCGTCACGGCGTCGAACGTCACCGGCGCTGCCGATTCTTGAGTGCCAACGATAAGGAGACCCCTAT    2430
                                ——— catR coding region ———
```

FIG. 3B-1

```
GTTCTGTCGCCTCTCTACTGTGGTCGGTTCCGTGGTAGTGTTGACACTGCGCCGTGATGTTCACGGTCACGCCTTGTCGGTTCTACACTGA    2520
         ——— catR coding region ———
CGAGGGTAACTATGGTATCTTGATATGGTCACCCAACAATAATTCAATACATGCTAACAGATATGTCTCTACTAGACATCGTCGGTATCA    2610
         ——— catR coding region ———
ATTTCGGCCCCCTTCATCCAGGACCGCCATCCAGTTCCCCGATCTTGTCCACGCCATCAAGCCCATGCCCAACAATGAGATCCCCCAGG    2700
         ——— catR coding region ———
CCGCTACTGCACACACTTCGCTTGGGACTCTTCAGCCAGCAGAGCACTGCCCTCCACAGTGCCTTGTGGCGTGATGTCTGGTAACGGTA    2790
         ——— catR coding region ———
TTCCTCGTTCTTTCCGCCACATGAACGGCTACGGAGTCCACAGCTTCCGCTTCGCGCCAATGGCACTTCCAAGGTGGTGCGAACAC    2880
         ——— catR coding region ———
CTTGGAAGTGCCAACAGGGTGTTGCCAGTCTGGTGTGGGATGAAGCTCAGCGCCCGCTGTGTAAGAACAGTGACTACCACCGCCAGGATC    2970
         ——— catR coding region ———
TGTACAAATGCGATGCCAATGGCCACTACCCGGAAATACGAGGTCAGCCAATCCCTGATGTCTATCGATAGACCCTTTTGCTGACAATCC    3060
         ——— catR coding region ———
CCTAGCTCCAAGCCCAGATCATGATGAGGCTGACACTTCGTTTCGGCTTCGACCTTCTGGATCCCCACCAAGTTGGTCCCCGAGGAGG    3150
         ——— catR coding region ———
TGTCCCTTACACTCCTCTCGGAATGATGAGCTCAATGCCAACCCCACCAACTACTTTGCTGAAGTTGAACAGGCTGGTGTATGTATTC    3240
         ——— catR coding region ———
```

FIG. 3B-2

| FIG. 3B-1 |
|-----------|
| FIG. 3B-2 |

CCCATTCATCAAATGCCAGACATAATCTAACTTCTGCAGTTCAACCCGGTCACGTGTTCCTGGCATTGACTTCACGGACCCCTG 3330
——— catR coding region ———

CTGCAAGGCCGTCTCTTCTCCTACCTGACACTCAGTTGACCCGTCACGGCCGGTCCCAACTTCGAGCAAATCCCGTCAACGTCCTCGC 3420
——— catR coding region ———

AAGCCCGTTCACAACAACAACCGTGACGGCCTTCGGGCAGCAGATCCCACCAACAACTGGGCCTACACCCCCAACAGCATGAGCAAC 3510
——— catR coding region ———

GGTTACCCCATGCAAGCCAACCAGACCCCAGGGTCATGGTTCTTCACCGCGCCCTACCGCTTCCGGCCATCTCGTCCGCCAGACC 3600
——— catR coding region ———

AGCCCGACCTTCAATGACCACTGGTCCCAGCCCGCCATGTTCTCTGGAACTCTCTGATCCCGCTGAGCAGCAGATGGTTGTCAACGGCATT 3690
——— catR coding region ———

GTCTTTGAGAACTCCAAGGTTAACAGCCCCACGTTCGGAAGAAACGTTGTCAACCAGCTGAAACATGTCAACAACCTCGCCGTCCGT 3780
——— catR coding region ———

GTCGCTCGGTGCTCTTGGTCTCGATGAGCCCTCCCCCAACCGACTTACTACACCCTCAACAAGACCTCAACGTCGGTACCTTCGGCAAG 3870
——— catR coding region ———

CCCCTCCTCAGCATCGAGGGTCTGCAGGTCGCAGGTCTTCCTGGCCTTCCTGGAACTCCCACCCCGAATCATCAAGCAGGCCAGGCCATGGCCGCGC 3960
——— catR coding region ———

AGTTCTCTGCCGCTGGCGTCGACCTGAGACATTGTCACGGAGCCTACGGCGATGGTGTCAACACCACTACGCCCTGTCTGATGCCATCG 4050
——— catR coding region ———

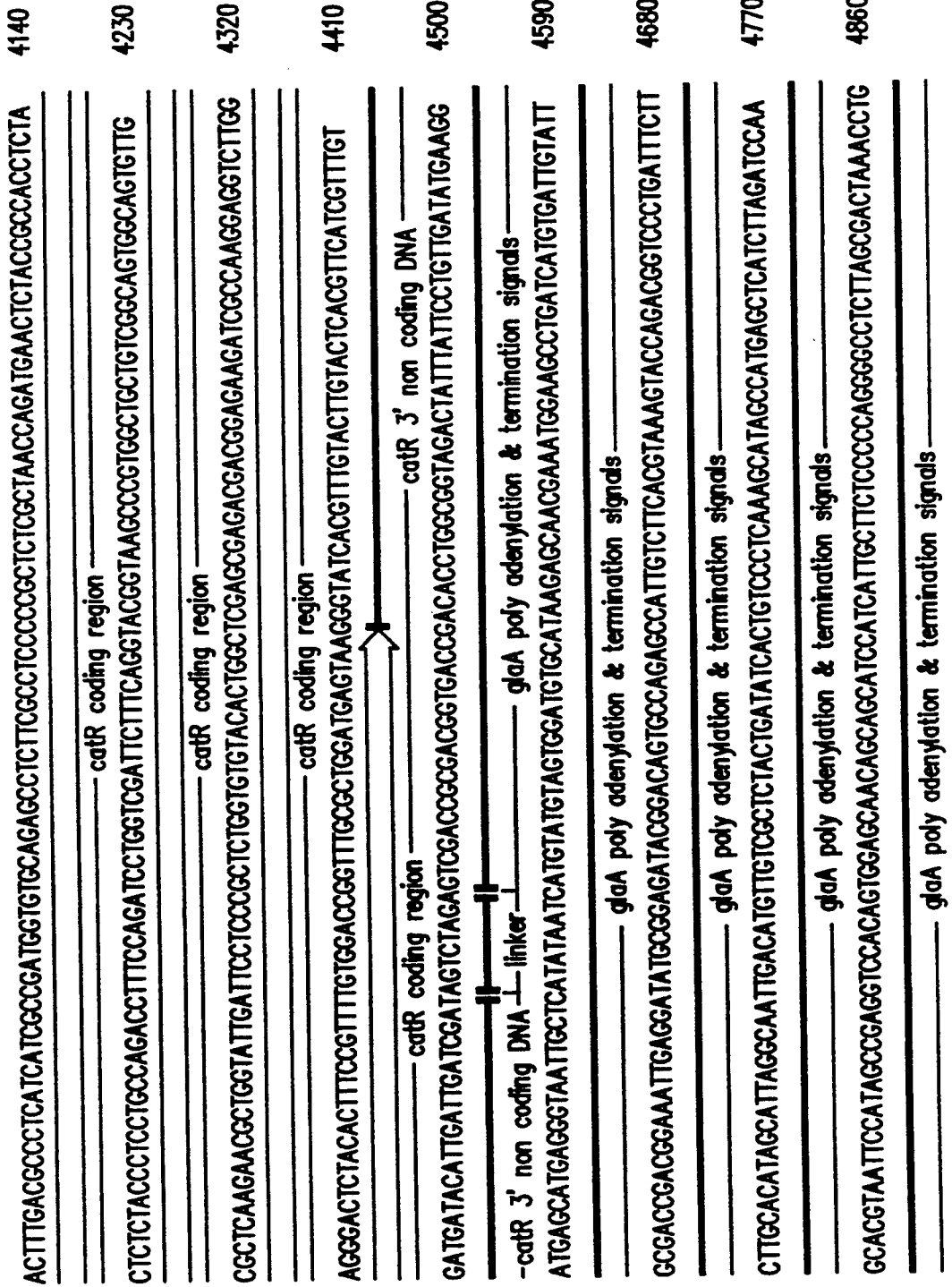

```
GAGTATGTCTCAACCAGCCAATGAATCGTCTTCGCTTCAATGTCCTTGACACTTCTGAGAGGGTCCCCATCCCTCAATGCTAATTCAAAA    4950
                                   ——— glaA poly adenylation & termination signals ———

TATAGCCGAGATGCATGGTGAGTCCAAAGTAGACAGTATTGCCGGAATGACGGGGCCAGTTGCCGCGAGTCATTGGCCGGCTGTGATG    5040
                                   ——— glaA poly adenylation & termination signals ———

CCATCTGCCACTAAATCGATCATTGATCCACCGCCCACGAGGGCCGGTCTTTGCCGTGCGTCCAGGTTCACACATCTCTCTC    5130
                                   ——— glaA poly adenylation & termination signals ———

TGCAGCTCCAGACTGACCAGACTATTCTACTTACTGCTCTGATCGGCTCCATCAGAGCTATGCCGTTATCCGTCCGTGCTGCGCCAT    5220
                                   ——— glaA poly adenylation & termination signals ———

CGGCTATCTTGATCGCGAGCTCGAACTCACTTCTCTTGTTTAATAGTTGTTCTCGTCGACTGAGTGTCGGTGACAGACCACAACACCA    5310
                                   ——— glaA poly adenylation & termination signals ———

TTGTTGCAGGGGGTAAATTTATTCAATTCAGGAATTGGATTGTTCGTCCCGGCCATGATGTTCTTGCCGCCTTTGTTGCCCTGTTTGTCG    5400
                                   ——— glaA poly adenylation & termination signals ———

GATGCGACGCCCTCGCTGTGCAGCAGGCAGGTACTGCTGGATGATGAGCCGTCGGTCTCCCCGCCAAGCCTAACTTCCTCTCTTCATTCTT    5490
                                   ——— glaA poly adenylation & termination signals ———

ACGGATGATGATCAGGATCTGCAGATCGAATTCCACCGGCGTATATCGCCGTATACACAGCCGAGAATCAAGGAGAAGGGTACTGAGTTTTGAA    5580
                                   ——— glaA poly adenylation & termination signals ———

TCATTTGTTACTACTGGCCTCTGTCGTCCGTCCGCGCGTGAGTCTTTGACGGAAGACAGGCCTCATAATACTAATGTGACGGATGTGAAC    5670
                                   ——— glaA poly adenylation & termination signals ———
```

FIG. 3D-1

```
CCGCCCTTATGTATGAATACCTCTCAGATCGGTCATGTTTCTCGGTGTAAAATTGCTAATGCAGCATAGCGGATACCCCAAGTTCGTC   5760
                                                ——— glaA poly adenylation & termination signals ———
GCCCAAGGCTTCAACGAAACTTCCTCCCCGTTGGCTGCAGTCCGCCCGGGTTACACAATACCTTCTACACGGGGAAACTGTTCAACTGCCAC   5850
   ——— glaA poly adenylation & termination signals ———
AGCGGTCGCTACCTATAATGCACCGTTTGTGAACGGCTTCAATGGCTCTCTGATTCCTCCTGATCCCCACACCTATTCCTACTGGAACGGCG   5940
   ——— glaA poly adenylation & termination signals ———
ACGTACCAACGAAACCATGAGCCTCCCGGAGCTACGAGGGACAATACACAACGGATGTGATCGGGAGAAGGCATCGGGGTTGTTGGCA   6030
   ——— glaA poly adenylation & termination signals ———
GATGCGCCTGGACAGGACACGCCCGTTCTTCTGACGGTCGCCTATCGCGCCGCCACGAACATCGATAAGCTTATCACCGTCCCTTATCAGCCA   6120
                                                                             ——— pyrG gene ———
CCCGTCGCCATTTGCTCTACGCCAAGAGTACCAGGACTAAGTACTTCGGCAGCCTGCCTTATCTGCATCAAATCGTCTACCGCCATTAATCCC   6210
——— pyrG gene ———
GTGCCACCCTATAATAGCCTGCAGGATCAATACCGTTTGACATCCGAGTCCGCGACTACCCGTGCTGACATTAGTTTGTATGC   6300
——— pyrG gene ———
GTATCGTAGCGGCAAGTTGCATTCTATATCATTCATAACCATCAAAACTTTTTCCTCATTTATAGTATTAGTTTCCGCCGACACGGG   6390
——— pyrG gene ———
CCAGGTACGCCCTCCCAACCTTCCTTCTGGTACTGTTGCGCCAGCCTCGGCCAGCCGGCGGTCCGGGCCGGGCGTAGATACCGCGTAGAATGA   6480
——— pyrG gene ———
```

FIG. 3D-2

| FIG. 3D-1 |
|-----------|
| FIG. 3D-2 |

```
AGTCAGCACCCGACCGATAGCCGATGCGGGAGTCTGGTACTGCTGACCGAGCTTATCTCCCTTGGACGAAATGTTCACACCAGTCGTGA    6570
                                    —— pyrG gene ——
AGACCACAAAGTCCTCCTCATCCGAAGGAGAGCTGACTTCCGACTGCACCTCACCCAACGAGCGGGTCGACACAAATCCATGACGAAGT    6660
                                    —— pyrG gene ——
TCTTGTATTTCCGGGCATAATCAACCGAAGAAGTAGTGTACTGGCCGGTGGCCAAGGAACCCTTAGAGGTCATTTCCGCCAAGATCAACA    6750
                                    —— pyrG gene ——
GACCACGTTCGGGGCCTAGGAGAAGTCCGGTGCAGACCCCGTCTGAGCGAGAGCCTCGACGAGGCCTCGCCAGGCAGGATGCTGCAGT    6840
                                    —— pyrG gene ——
TGATGATATGGGCCCATTCTGAGATCGGGAGGTACCACGGTGGAGTATTGCTTCTGGACAGTGTTGCCAATGTCGATGAATTTGCGGTCCT    6930
                                    —— pyrG gene ——
CGAAGATGAGGAAGTGTGTCTGCGCAAGAGCCTTGAGCCCTCAATGCTCTGTCGCTGAAGTCAGAGAGGATATCGATGTGGGTTT    7020
                                    —— pyrG gene ——
TGATCACGGGCGATGTAGGGACCGAGACCTCAGTCGGTATCCCGGTTAATAAGTTGTATGCAGCATAAACAGGCAGAATGGCGGGTCGG    7110
                                    —— pyrG gene ——
CCTACGGGTCAGCAAGAGTCTAGTAGCTCCTTAGTGGTGGTAACGTCGGCAGAGACGGTCACATTGGTCTTCTTGGCCCTTCAGCAATTTCGAA    7200
                                    —— pyrG gene ——
CAGCCGCTTGGCCAGAGCATTGGGGTGCTTGCTGGCACGGGCAGTGTAGTTGCAATTGCGACTTGGAGGACATGGTGTCGGTGGAGGGTT    7290
                                    —— pyrG gene ——
```

```
AATGCGGGGATGAAAGAGCCTTGTGTCAATATGAGTAGCTTGGAGTTTCGACTGATAGGCCCTAATTGGTAGATCCAGAGATGCGCAAATA    7380
                                  ——— pyrG gene ———

CTACCGAATAATTTAGGACGGACTGGCCCTTATATGAGGTGAACAATGCACATTCGAGCAAAAGAGGACTCAGTAAATCATCG            7470
                                  ——— pyrG gene ———

CGACCCTCCACGCACCAGCCACATCGGGTGATTTCGCCGCTCCGGAACCGTGGGGTTCAGCCACACCTGCAAAGGCAGTTCCTTT          7560
                                  ——— pyrG gene ———

CCATTGAAGTTGCCACACACCCAGGTTCATTGGAGCTCGTATTTTTCCCTGCTGCACATGGGGAAATAGACCAGTCAATCAGAAAGCCATT   7650
                                  ——— pyrG gene ———

GTCATTCCCGACCCTAGCAGTAGTACCGATATAAACCGGTCGTGTGGAGTAGTAATATACAAGTGAGAAATTTATTACATATAGCGTGGTATAG 7740
                                  ——— pyrG gene ———

CCAACAGCGCCAATCACACCCGACGAAGTCAATCCAAACTTTAAAAGGTAGGGAAATCAACTCCCTCGCGACTTCCAAAAGAGGTCAAT     7830
                                  ——— pyrG gene ———

CCCCAAAGAGCTCCCTGTGCAAGCAAGTAGAAGCTGCCGGACCGACCCCGGCTTGCCGGAGTACACGTATCCGTAAAGGAAC             7920
                                  ——— pyrG gene ———

AGTGAGCCGACCGGAGAACCCAAATGCTTCCAAGGCCAGTTGCCAACTGGGCGTACTTCAATCCAGCACCAGGATGAAGAGCATAGTTTGG   8010
                                  ——— pyrG gene ———

CTGGAGTTCTCAAGGAAGTTGGCCATGAGCGGTGAGCGGAGTTAACTGCTCAGCCCTTGGGCTGCACGATTGAATGTATGTTAGCTCGAGGAA 8100
                                  ——— pyrG gene ———
```

| FIG. 3E-1 |
|-----------|
| FIG. 3E-2 |

SEQUENCE LISTING ( 1 ) GENERAL INFORMATION:

(i i i) NUMBER OF SEQUENCES: 9

(2) INFORMATION FOR SEQ ID NO:1:

(i) SEQUENCE CHARACTERISTICS:
        (A) LENGTH: 29 base pairs
        (B) TYPE: nucleic acid
        (C) STRANDEDNESS: both
        (D) TOPOLOGY: linear (i i) MOLECULE TYPE: DNA (genomic)

(x i) SEQUENCE DESCRIPTION: SEQ ID NO:1:

```
GATCAGATCT GGATCCATCG ATAGTCTAG                                  29
```

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: both
        (D) TOPOLOGY: linear (i i) MOLECULE TYPE: DNA (genomic)

(x i) SEQUENCE DESCRIPTION: SEQ ID NO:2:

```
GATCTCAGCA ATGCGTC                                               17
```

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: both
        (D) TOPOLOGY: linear (i i) MOLECULE TYPE: DNA (genomic)

(x i) SEQUENCE DESCRIPTION: SEQ ID NO:3:

```
AAAACCGTTT AAACGGCGCG CCTTAATTAA GGAAAA                          36
```

(2) INFORMATION FOR SEQ ID NO:4:

(i) SEQUENCE CHARACTERISTICS:
        (A) LENGTH: 3107 base pairs
        (B) TYPE: nucleic acid
        (C) STRANDEDNESS: double
        (D) TOPOLOGY: linear (i x) FEATURE:
        (A) NAME/KEY: CDS
        (B) LOCATION: join(327..620, 683..907, 969..1385, 1440..1604,
            1654..2745)

(x i) SEQUENCE DESCRIPTION: SEQ ID NO:4:

```
CTTGTCACCG AGTGCCCGTT TGTCACTTGT TGTGGTGATC TTGAGCACAT CGCGTTCCTC    60

TCGTCTCATC ACATCGAGTG ATCAACATTG CATGACCCTA GTGGAGCCCC TTCGTCTCCC   120

AACAGGAGGG TCCGGATTAC CAAGTCCCGA CACCGTTTGG CTGTAATTCG ACTCAAATTC   180

TGGATTCGTA GCTTAACTAA GACGCGTGGT CTGTTAACCG GCCTCGCCAT GGATGCCGAT   240

ATAAGGACCC TAGGGGACTC CCCCCTGGTG ACTCTCGTCG AAGATCGCA GCACTCTGAA    300

TTCTCCTAGT CTTCGTTTAC TCCGCC ATG CGT CAT TTC TGG CTT TTG CCA GCT   353
                            Met Arg His Phe Trp Leu Leu Pro Ala
                              1               5

GTT GCT GGT ATC GCT GGG GCT CAA TGC CCC TAC CTG TCG GGT GAA ATG    401
Val Ala Gly Ile Ala Gly Ala Gln Cys Pro Tyr Leu Ser Gly Glu Met
 10              15              20              25
```

| | | | | | | | | | | | | | | | | |
|---|---|---|---|---|---|---|---|---|---|---|---|---|---|---|---|---|
| AGT | TTC | ACC | CAG | GAG | CAG | GAC | AAT | GCT | GGC | GAT | ACC | ATT | GAG | GTC | ACG | 449 |
| Ser | Phe | Thr | Gln | Glu | Gln | Asp | Asn | Ala | Gly | Asp | Thr | Ile | Glu | Val | Thr | |
| | | | 30 | | | | | 35 | | | | | | 40 | | |
| GAG | CAG | CCC | ATT | GAC | AAC | ACC | CTG | TAT | GTC | AAT | GAC | ACC | GGT | AGC | TAC | 497 |
| Glu | Gln | Pro | Ile | Asp | Asn | Thr | Leu | Tyr | Val | Asn | Asp | Thr | Gly | Ser | Tyr | |
| | | | 45 | | | | | 50 | | | | | 55 | | | |
| ATG | ACT | ACC | GAC | TTT | GGC | ACT | CCG | ATC | TCC | GAC | CAG | ACC | AGT | CTC | AAG | 545 |
| Met | Thr | Thr | Asp | Phe | Gly | Thr | Pro | Ile | Ser | Asp | Gln | Thr | Ser | Leu | Lys | |
| | 60 | | | | | 65 | | | | | 70 | | | | | |
| GCC | GGG | CCC | CGT | GGT | CCT | ACC | CTG | TTG | GAG | GAC | TTT | ATC | TTC | CGT | CAG | 593 |
| Ala | Gly | Pro | Arg | Gly | Pro | Thr | Leu | Leu | Glu | Asp | Phe | Ile | Phe | Arg | Gln | |
| | 75 | | | | | 80 | | | | | 85 | | | | | |
| AAG | CTT | CAG | CGG | TTC | GAC | CAT | GAG | CGT | GTAAGTACAG | TAACTGCTGC | | | | | | 640 |
| Lys | Leu | Gln | Arg | Phe | Asp | His | Glu | Arg | | | | | | | | |
| 90 | | | | | 95 | | | | | | | | | | | |

GGTGTGTAGT AACAATAAAT TGACCCAGTG GTTTTCAATT AG GTC CCC GAG CGC 694

| | | | |
|---|---|---|---|
| Val | Pro | Glu | Arg |
| 100 | | | |

| | | | | | | | | | | | | | | | | |
|---|---|---|---|---|---|---|---|---|---|---|---|---|---|---|---|---|
| GTC | GTC | CAC | GCC | CGT | GGT | GCC | GGT | GCA | TAT | GGT | ACT | TTC | AAA | TCC | TAC | 742 |
| Val | Val | His | Ala | Arg | Gly | Ala | Gly | Ala | Tyr | Gly | Thr | Phe | Lys | Ser | Tyr | |
| | | 105 | | | | | 110 | | | | | 115 | | | | |
| GCC | GAC | TGG | TCG | AAC | GTC | ACG | GCT | GCC | GAT | TTC | TTG | AGT | GCC | AAC | GAT | 790 |
| Ala | Asp | Trp | Ser | Asn | Val | Thr | Ala | Ala | Asp | Phe | Leu | Ser | Ala | Asn | Asp | |
| | 120 | | | | | 125 | | | | | 130 | | | | | |
| AAG | GAG | ACC | CCT | ATG | TTC | TGT | CGC | TTC | TCT | ACT | GTG | GTC | GGT | TTC | CGT | 838 |
| Lys | Glu | Thr | Pro | Met | Phe | Cys | Arg | Phe | Ser | Thr | Val | Val | Gly | Phe | Arg | |
| 135 | | | | | 140 | | | | | 145 | | | | | 150 | |
| GGT | AGT | GTT | GAC | ACT | GCG | CGT | GAT | GTT | CAC | GGT | CAC | GCT | TGT | CGG | TTC | 886 |
| Gly | Ser | Val | Asp | Thr | Ala | Arg | Asp | Val | His | Gly | His | Ala | Cys | Arg | Phe | |
| | | | | 155 | | | | | 160 | | | | | 165 | | |
| TAC | ACT | GAC | GAG | GGT | AAC | TAT | GGTATCTTGA | TATGGTCACC | CAACAATAAT | | | | | | | 937 |
| Tyr | Thr | Asp | Glu | Gly | Asn | Tyr | | | | | | | | | | |
| | | | | 170 | | | | | | | | | | | | |

TCAATACATG CTAACAGATA TGTCTCTACT A GAC ATC GTC GGT ATC AAT TTC 989

| | | | | | |
|---|---|---|---|---|---|
| Asp | Ile | Val | Gly | Ile | Asn | Phe |
| 175 | | | | | 180 |

| | | | | | | | | | | | | | | | | |
|---|---|---|---|---|---|---|---|---|---|---|---|---|---|---|---|---|
| GCC | CCC | TTC | TTC | ATC | CAG | GAC | GCC | ATC | CAG | TTC | CCC | GAT | CTT | GTC | CAC | 1037 |
| Ala | Pro | Phe | Phe | Ile | Gln | Asp | Ala | Ile | Gln | Phe | Pro | Asp | Leu | Val | His | |
| | | | | 185 | | | | | 190 | | | | | 195 | | |
| GCC | ATC | AAG | CCC | ATG | CCC | AAC | AAT | GAG | ATC | CCC | CAG | GCC | GCT | ACT | GCA | 1085 |
| Ala | Ile | Lys | Pro | Met | Pro | Asn | Asn | Glu | Ile | Pro | Gln | Ala | Ala | Thr | Ala | |
| | | 200 | | | | | 205 | | | | | 210 | | | | |
| CAC | ACT | TCC | GCT | TGG | GAC | TTC | TTC | AGC | CAG | CAG | AGC | ACT | GCC | CTC | CAC | 1133 |
| His | Thr | Ser | Ala | Trp | Asp | Phe | Phe | Ser | Gln | Gln | Ser | Thr | Ala | Leu | His | |
| | | 215 | | | | | 220 | | | | | 225 | | | | |
| AGT | GCC | TTG | TGG | CTG | ATG | TCT | GGT | AAC | GGT | ATT | CCT | CGT | TCT | TTC | CGC | 1181 |
| Ser | Ala | Leu | Trp | Leu | Met | Ser | Gly | Asn | Gly | Ile | Pro | Arg | Ser | Phe | Arg | |
| 230 | | | | | 235 | | | | | 240 | | | | | | |
| CAC | ATG | AAC | GGC | TAC | GGA | GTC | CAC | AGC | TTC | CGC | TTC | GTC | GCT | GCC | AAT | 1229 |
| His | Met | Asn | Gly | Tyr | Gly | Val | His | Ser | Phe | Arg | Phe | Val | Ala | Ala | Asn | |
| 245 | | | | 250 | | | | | 255 | | | | | | 260 | |
| GGC | ACT | TCC | AAG | GTG | GTG | CGA | ACA | CCT | TGG | AAG | TCC | CAA | CAG | GGT | GTT | 1277 |
| Gly | Thr | Ser | Lys | Val | Val | Arg | Thr | Pro | Trp | Lys | Ser | Gln | Gln | Gly | Val | |
| | | | | 265 | | | | | 270 | | | | | 275 | | |
| GCC | AGT | CTG | GTG | TGG | GAT | GAA | GCT | CAG | GCC | GCT | GCT | GGT | AAG | AAC | AGT | 1325 |
| Ala | Ser | Leu | Val | Trp | Asp | Glu | Ala | Gln | Ala | Ala | Ala | Gly | Lys | Asn | Ser | |
| | | | 280 | | | | | 285 | | | | | 290 | | | |
| GAC | TAC | CAC | CGC | CAG | GAT | CTG | TAC | AAT | GCG | ATG | CCC | AAT | GGC | CAC | TAC | 1373 |
| Asp | Tyr | His | Arg | Gln | Asp | Leu | Tyr | Asn | Ala | Met | Pro | Asn | Gly | His | Tyr | |
| | | 295 | | | | | 300 | | | | | 305 | | | | |

```
CCG AAA TAC GAG  GTCAGCCAAT CCCTTGATGT CTATCGATAG AGCCTTTTGC           1425
Pro Lys Tyr Glu
        310

TGACAATCCC CTAG CTC CAA GCC CAG ATC ATG GAT GAG GCT GAC ATG CTT        1475
                Leu Gln Ala Gln Ile Met Asp Glu Ala Asp Met Leu
                            315             320

CGT TTC GGC TTC GAC CTT CTG GAT CCC ACC AAG TTG GTC CCC GAG GAG        1523
Arg Phe Gly Phe Asp Leu Leu Asp Pro Thr Lys Leu Val Pro Glu Glu
325             330             335                         340

GTT GTC CCT TAC ACT CCT CTC GGA ATG ATG GAG CTC AAT GCC AAC CCC        1571
Val Val Pro Tyr Thr Pro Leu Gly Met Met Glu Leu Asn Ala Asn Pro
                345             350                     355

ACC AAC TAC TTT GCT GAA GTT GAA CAG GCT GGT GTATGTATTC CCCATTCATC      1624
Thr Asn Tyr Phe Ala Glu Val Glu Gln Ala Gly
            360             365

AAATGCCAGA CATAATCTAA CTTCTGCAG TTC CAA CCC GGT CAC GTC GTT CCT        1677
                                Phe Gln Pro Gly His Val Val Pro
                                        370             375

GGC ATT GAC TTC ACC GAC GAC CCC CTG CTG CAA GGC CGT CTC TTC TCC        1725
Gly Ile Asp Phe Thr Asp Asp Pro Leu Leu Gln Gly Arg Leu Phe Ser
                380             385             390

TAC CTC GAC ACT CAG TTG ACC CGT CAC GGC GGT CCC AAC TTC GAG CAA        1773
Tyr Leu Asp Thr Gln Leu Thr Arg His Gly Gly Pro Asn Phe Glu Gln
            395             400             405

ATC CCC GTC AAC CGT CCT CGC AAG CCC GTT CAC AAC AAC AAC CGT GAC        1821
Ile Pro Val Asn Arg Pro Arg Lys Pro Val His Asn Asn Asn Arg Asp
        410             415             420

GGC TTC GGC CAG CAG CAG ATC CCC ACC AAC AAC TGG GCC TAC ACC CCC        1869
Gly Phe Gly Gln Gln Gln Ile Pro Thr Asn Asn Trp Ala Tyr Thr Pro
425             430             435

AAC AGC ATG AGC AAC GGT TAC CCC ATG CAA GCC AAC CAG ACC CAG GGT        1917
Asn Ser Met Ser Asn Gly Tyr Pro Met Gln Ala Asn Gln Thr Gln Gly
440             445             450             455

CAT GGT TTC TTC ACC GCG CCC TAC CGC TAC GCT TCC GGC CAT CTC GTC        1965
His Gly Phe Phe Thr Ala Pro Tyr Arg Tyr Ala Ser Gly His Leu Val
                460             465             470

CGC CAG ACC AGC CCG ACC TTC AAT GAC CAC TGG TCC CAG CCC GCC ATG        2013
Arg Gln Thr Ser Pro Thr Phe Asn Asp His Trp Ser Gln Pro Ala Met
            475             480             485

TTC TGG AAC TCT CTG ATC CCC GCT GAG CAG CAG ATG GTT GTC AAC GCC        2061
Phe Trp Asn Ser Leu Ile Pro Ala Glu Gln Gln Met Val Val Asn Ala
        490             495             500

ATT GTC TTT GAG AAC TCC AAG GTT AAC AGC CCC CAC GTT CGG AAG AAC        2109
Ile Val Phe Glu Asn Ser Lys Val Asn Ser Pro His Val Arg Lys Asn
505             510             515

GTT GTC AAC CAG CTG AAC ATG GTC AAC AAC AAC CTC GCC GTC CGT GTC        2157
Val Val Asn Gln Leu Asn Met Val Asn Asn Asn Leu Ala Val Arg Val
520             525             530             535

GCT CGT GGT CTT GGT CTC GAT GAG CCC TCC CCC AAC CCG ACT TAC TAC        2205
Ala Arg Gly Leu Gly Leu Asp Glu Pro Ser Pro Asn Pro Thr Tyr Tyr
                540             545             550

ACC TCC AAC AAG ACC TCC AAC GTC GGT ACC TTC GGC AAG CCC CTC CTC        2253
Thr Ser Asn Lys Thr Ser Asn Val Gly Thr Phe Gly Lys Pro Leu Leu
            555             560             565

AGC ATC GAG GGT CTG CAG GTC GGC TTC CTG GCC TCG AAC TCC CAC CCC        2301
Ser Ile Glu Gly Leu Gln Val Gly Phe Leu Ala Ser Asn Ser His Pro
        570             575             580

GAA TCC ATC AAG CAG GGC CAG GCC ATG GCC GCG CAG TTC TCT GCC GCT        2349
Glu Ser Ile Lys Gln Gly Gln Ala Met Ala Ala Gln Phe Ser Ala Ala
585             590             595
```

```
GGC GTC GAC CTG AAC ATT GTC ACC GAG GCC TAC GCC GAT GGT GTC AAC        2397
Gly Val Asp Leu Asn Ile Val Thr Glu Ala Tyr Ala Asp Gly Val Asn
600             605             610             615

ACC ACC TAC GCC CTG TCT GAT GCC ATC GAC TTT GAC GCC CTC ATC ATC        2445
Thr Thr Tyr Ala Leu Ser Asp Ala Ile Asp Phe Asp Ala Leu Ile Ile
                620             625             630

GCC GAT GGT GTG CAG AGC CTC TTC GCC TCC CCC GCT CTC GCT AAC CAG        2493
Ala Asp Gly Val Gln Ser Leu Phe Ala Ser Pro Ala Leu Ala Asn Gln
            635             640             645

ATG AAC TCT ACC GCC ACC TCT ACT CTC TAC CCT CCT GCC AGA CCT TTC        2541
Met Asn Ser Thr Ala Thr Ser Thr Leu Tyr Pro Pro Ala Arg Pro Phe
        650             655             660

CAG ATC CTG GTC GAT TCT TTC AGG TAC GGT AAG CCC GTG GCT GCT GTC        2589
Gln Ile Leu Val Asp Ser Phe Arg Tyr Gly Lys Pro Val Ala Ala Val
    665             670             675

GGC AGT GGC AGT GTT GCG CTC AAG AAC GCT GGT ATT GAT TCC TCC CGC        2637
Gly Ser Gly Ser Val Ala Leu Lys Asn Ala Gly Ile Asp Ser Ser Arg
680             685             690             695

TCT GGT GTG TAC ACT GGC TCG AGC GAG ACG ACG GAG AAG ATC GCC AAG        2685
Ser Gly Val Tyr Thr Gly Ser Ser Glu Thr Thr Glu Lys Ile Ala Lys
                700             705             710

GAG GTC TTG GAG GGA CTC TAC ACT TTC CGT TTT GTG GAC CGG TTT GCG        2733
Glu Val Leu Glu Gly Leu Tyr Thr Phe Arg Phe Val Asp Arg Phe Ala
            715             720             725

CTG GAT GAG TAAGGGTATC ACGTTTGTAC TTGTACTCAC GTTCATCGTT               2782
Leu Asp Glu
        730

TGTGATGATA CATTGATTGA TCGATAGATA TTTTGTGAGA TAGATAGAGT ATACTAGAGW      2842

GKACATATCT CTACTGATGA GGTGTTGTGC TGCTGCAACA CATATTTATG AATATATATT      2902

CTCTTCTTTG TGAAAGCTAG CCTTCTATAT AATCAGCAAT GGTTAACTCT TCCAATTCTA      2962

TAGATACCAA TCACCTAACC CACTCGGAAT GACGACAGAA AACATCGACA TGTTCGCCCA      3022

AGTAAAGCTA CTTGAACTTC TACATTTATG CTATGCTGGA GTCCTCTCAT AAGTCCAGAA      3082

TAAACAAAGA GATCCGATCC TGCTC                                            3107
```

( 2 ) INFORMATION FOR SEQ ID NO:5:

( i ) SEQUENCE CHARACTERISTICS:
        ( A ) LENGTH: 730 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Arg His Phe Trp Leu Leu Pro Ala Val Ala Gly Ile Ala Gly Ala
1               5              10              15

Gln Cys Pro Tyr Leu Ser Gly Glu Met Ser Phe Thr Gln Glu Gln Asp
            20              25              30

Asn Ala Gly Asp Thr Ile Glu Val Thr Glu Gln Pro Ile Asp Asn Thr
        35              40              45

Leu Tyr Val Asn Asp Thr Gly Ser Tyr Met Thr Thr Asp Phe Gly Thr
    50              55              60

Pro Ile Ser Asp Gln Thr Ser Leu Lys Ala Gly Pro Arg Gly Pro Thr
65              70              75              80

Leu Leu Glu Asp Phe Ile Phe Arg Gln Lys Leu Gln Arg Phe Asp His
            85              90              95

Glu Arg Val Pro Glu Arg Val Val His Ala Arg Gly Ala Gly Ala Tyr
        100             105             110
```

-continued

| | | | | | | | | | | | | | | |
|---|---|---|---|---|---|---|---|---|---|---|---|---|---|---|
| Gly | Thr | Phe 115 | Lys | Ser | Tyr | Ala | Asp 120 | Trp | Ser | Asn | Val 125 | Ala | Ala | Asp |
| Phe 130 | Leu | Ser | Ala | Asn | Asp | Lys 135 | Glu | Thr | Pro | Met | Phe 140 | Cys | Arg | Phe | Ser |
| Thr 145 | Val | Val | Gly | Phe | Arg 150 | Gly | Ser | Val | Asp | Thr 155 | Ala | Arg | Asp | Val | His 160 |
| Gly | His | Ala | Cys | Arg 165 | Phe | Tyr | Thr | Asp | Gly 170 | Asn | Tyr | Asp | Ile 175 | Val |
| Gly | Ile | Asn | Phe 180 | Ala | Pro | Phe | Phe | Ile 185 | Gln | Asp | Ala | Ile | Gln 190 | Phe | Pro |
| Asp | Leu | Val 195 | His | Ala | Ile | Lys | Pro 200 | Met | Pro | Asn | Asn | Glu 205 | Ile | Pro | Gln |
| Ala | Ala 210 | Thr | Ala | His | Thr | Ser 215 | Ala | Trp | Asp | Phe | Phe 220 | Ser | Gln | Gln | Ser |
| Thr 225 | Ala | Leu | His | Ser | Ala 230 | Leu | Trp | Leu | Met | Ser 235 | Gly | Asn | Gly | Ile | Pro 240 |
| Arg | Ser | Phe | Arg | His 245 | Met | Asn | Gly | Tyr | Gly 250 | Val | His | Ser | Phe | Arg 255 | Phe |
| Val | Ala | Ala | Asn 260 | Gly | Thr | Ser | Lys | Val 265 | Val | Arg | Thr | Pro | Trp 270 | Lys | Ser |
| Gln | Gln | Gly 275 | Val | Ala | Ser | Leu | Val 280 | Trp | Asp | Glu | Ala | Gln 285 | Ala | Ala | Ala |
| Gly | Lys 290 | Asn | Ser | Asp | Tyr | His 295 | Arg | Gln | Asp | Leu | Tyr 300 | Asn | Ala | Met | Pro |
| Asn 305 | Gly | His | Tyr | Pro | Lys 310 | Tyr | Glu | Leu | Gln | Ala 315 | Gln | Ile | Met | Asp | Glu 320 |
| Ala | Asp | Met | Leu | Arg 325 | Phe | Gly | Phe | Asp | Leu 330 | Leu | Asp | Pro | Thr | Lys 335 | Leu |
| Val | Pro | Glu | Glu 340 | Val | Val | Pro | Tyr | Thr 345 | Pro | Leu | Gly | Met | Met 350 | Glu | Leu |
| Asn | Ala | Asn | Pro 355 | Thr | Asn | Tyr | Phe | Ala 360 | Glu | Val | Glu | Gln 365 | Ala | Gly | Phe |
| Gln | Pro | Gly 370 | His | Val | Val | Pro | Gly 375 | Ile | Asp | Phe | Thr | Asp 380 | Asp | Pro | Leu |
| Leu 385 | Gln | Gly | Arg | Leu | Phe 390 | Ser | Tyr | Leu | Asp | Thr 395 | Gln | Leu | Thr | Arg | His 400 |
| Gly | Gly | Pro | Asn | Phe 405 | Glu | Gln | Ile | Pro | Val 410 | Asn | Arg | Pro | Arg | Lys 415 | Pro |
| Val | His | Asn | Asn 420 | Asn | Arg | Asp | Gly | Phe 425 | Gly | Gln | Gln | Gln | Ile 430 | Pro | Thr |
| Asn | Asn | Trp 435 | Ala | Tyr | Thr | Pro | Asn 440 | Ser | Met | Ser | Asn | Gly 445 | Tyr | Pro | Met |
| Gln | Ala 450 | Asn | Gln | Thr | Gln | Gly 455 | His | Gly | Phe | Phe | Thr 460 | Ala | Pro | Tyr | Arg |
| Tyr 465 | Ala | Ser | Gly | His | Leu 470 | Val | Arg | Gln | Thr | Ser 475 | Pro | Thr | Phe | Asn | Asp 480 |
| His | Trp | Ser | Gln | Pro 485 | Ala | Met | Phe | Trp | Asn 490 | Ser | Leu | Ile | Pro | Ala 495 | Glu |
| Gln | Gln | Met | Val 500 | Val | Asn | Ala | Ile | Val 505 | Phe | Glu | Asn | Ser | Lys 510 | Val | Asn |
| Ser | Pro | His 515 | Val | Arg | Lys | Asn | Val 520 | Val | Asn | Gln | Leu | Asn 525 | Met | Val | Asn |
| Asn | Asn 530 | Leu | Ala | Val | Arg | Val 535 | Ala | Arg | Gly | Leu | Gly 540 | Leu | Asp | Glu | Pro |
| Ser | Pro | Asn | Pro | Thr | Tyr | Tyr | Thr | Ser | Asn | Lys | Thr | Ser | Asn | Val | Gly |

| | 545 | | | | 550 | | | | 555 | | | | 560 | |
|---|---|---|---|---|---|---|---|---|---|---|---|---|---|---|
| Thr | Phe | Gly | Lys | Pro | Leu | Leu | Ser | Ile | Glu | Gly | Leu | Gln | Val | Gly | Phe |
| | | | | 565 | | | | | 570 | | | | | 575 | |

| Leu | Ala | Ser | Asn | Ser | His | Pro | Glu | Ser | Ile | Lys | Gln | Gly | Gln | Ala | Met |
|---|---|---|---|---|---|---|---|---|---|---|---|---|---|---|---|
| | | | 580 | | | | | 585 | | | | | 590 | | |

| Ala | Ala | Gln | Phe | Ser | Ala | Ala | Gly | Val | Asp | Leu | Asn | Ile | Val | Thr | Glu |
|---|---|---|---|---|---|---|---|---|---|---|---|---|---|---|---|
| | | | 595 | | | | 600 | | | | | 605 | | | |

| Ala | Tyr | Ala | Asp | Gly | Val | Asn | Thr | Thr | Tyr | Ala | Leu | Ser | Asp | Ala | Ile |
|---|---|---|---|---|---|---|---|---|---|---|---|---|---|---|---|
| | 610 | | | | | 615 | | | | | 620 | | | | |

| Asp | Phe | Asp | Ala | Leu | Ile | Ile | Ala | Asp | Gly | Val | Gln | Ser | Leu | Phe | Ala |
|---|---|---|---|---|---|---|---|---|---|---|---|---|---|---|---|
| 625 | | | | | 630 | | | | | 635 | | | | | 640 |

| Ser | Pro | Ala | Leu | Ala | Asn | Gln | Met | Asn | Ser | Thr | Ala | Thr | Ser | Thr | Leu |
|---|---|---|---|---|---|---|---|---|---|---|---|---|---|---|---|
| | | | | 645 | | | | | 650 | | | | | 655 | |

| Tyr | Pro | Pro | Ala | Arg | Pro | Phe | Gln | Ile | Leu | Val | Asp | Ser | Phe | Arg | Tyr |
|---|---|---|---|---|---|---|---|---|---|---|---|---|---|---|---|
| | | | 660 | | | | | 665 | | | | | 670 | | |

| Gly | Lys | Pro | Val | Ala | Ala | Val | Gly | Ser | Gly | Ser | Val | Ala | Leu | Lys | Asn |
|---|---|---|---|---|---|---|---|---|---|---|---|---|---|---|---|
| | | 675 | | | | | 680 | | | | | 685 | | | |

| Ala | Gly | Ile | Asp | Ser | Ser | Arg | Ser | Gly | Val | Tyr | Thr | Gly | Ser | Ser | Glu |
|---|---|---|---|---|---|---|---|---|---|---|---|---|---|---|---|
| | 690 | | | | | 695 | | | | | 700 | | | | |

| Thr | Thr | Glu | Lys | Ile | Ala | Lys | Glu | Val | Leu | Glu | Gly | Leu | Tyr | Thr | Phe |
|---|---|---|---|---|---|---|---|---|---|---|---|---|---|---|---|
| 705 | | | | | 710 | | | | | 715 | | | | | 720 |

| Arg | Phe | Val | Asp | Arg | Phe | Ala | Leu | Asp | Glu |
|---|---|---|---|---|---|---|---|---|---|
| | | | | 725 | | | | | 730 |

( 2 ) INFORMATION FOR SEQ ID NO:6:

( i ) SEQUENCE CHARACTERISTICS:
        ( A ) LENGTH: 8533 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

```
GCGGCCGCCT CGAGGATTGT CTGAACATTG ACATTCGGCG CCCAGCGAAC CCCAACTGCG      60
GACGCGAATG CCCGTGCTGG TCTCGGATCT TTGGCGGAGG CTTTGAACTT GGTTCAAAGG     120
CCATGTATGA CGGCACAACG ATGGTATCAT CGTCGATAGA CAAGAATATG CCTATCGTGT     180
TTGTAGCGAT GAACTATCGC GTAGGGGGCT TCGGGTTTCT GCCCGGAAAG GAGATTCTGG     240
AGGACGGGTC CGCCAACTTA GGTCTTTGAC CAAGCCTTGC CCTAGTGGGT GGCCGACAAC     300
ATCGAGGCGT TGGTGGAGA CCAGACAAGG TGACAATCTG GGGAGAATCA GCAGGGGCTA     360
TTTCTGTCTT GATCAGATGA TCTGTACGAC GGAAACATCG CTTACAAGGA CAAGCCCTTG     420
TTTCGGGAGC CATCATGGAC TCCGGTATGT GTTCCCGCAG ACCCTGTCGA CGGGGTCAAG     480
GGATCAGCAA GTATATGATG CGGTTGTGGA CTCTGCAGGC TGTTCCTCTT CCAACGACAC     540
CCTGGCTTGT CTGCGTGAGC TAGACTACAC CGACTATCTC AATGCGGCAA ACTCGTGCCG     600
GGGATCCTAG GTTATCACCG TGGCGCTATC ATATGTGCCT CGACCAGACG GGACGGCATT     660
TGTCGGCGTC GCCAGATTTT GGGTAAAGCA GGAAGTATG CGCGGGTCCC ATTCATCGTG     720
GGCGACCAAG AGGATGAGGG GACCTTGTTC GCCTTGTTTC AGTCCTTACG ACGATCGACG     780
AGGTAGTCGA CTATCTGGGC ACCTACTTCT TCTATGACGC TAGCCAGGAG CAGCTTGAAG     840
AATTAGTGGC CCTGTACCCA GACACCACCA CATATGGGTC TCCCTTCAGG ACGGGCAGGC     900
CAACAACTGG TATCCGCAAT TTAAGCGATT GGCCGCCATT CTCGGCGACT TGGTCTTCAC     960
CATTACCCGG CGGCATTCCT GTCATATGCA GAGGAGCTCT CCCCTGACCT CCCGAAATGG    1020
```

```
TCGTACCTGG CGACCTATGA CTATGGCAGC CAATTCTGGG GACCTTCCAT GGAAGTGACC    1080

TGCTGCAGGT GTTCTATGGG ATCAAGCCGA ACTATGCAGC GAGTTCCAGC CACACGTATT    1140

ATCTGAGTTT TGTATACACG CTGGATCCGA ACTCCAATCG GGGGAGTAC ATGGAATGGC     1200

CCCAGTGGCA GCCGACAGTT GATGAATTTC GGAGCGAACA GCAGTCTCCT TACGGATGAT   1260

TTCCGCAACG GGACATATGA GTTCATCCTG CAGAATACCG CGGCGTTCCA CATCTGATGC   1320

CATTCGGGAG GGGTCCGGAG GTCAGGGACT AGCCTTATGA ACGTAATGAT GGAAGTGTCT   1380

GGCCTCGGCA AAGGATATAT AGGGTCATAA TAAGTAGTAC TAGTTATATT AATGGAAGGG   1440

TATATACCAC GCGTTGGACC TTGGGACCTG CATTATAGCT TCCCGTTAGG TATAATTACC   1500

GTTGTTATAG CAGCCAATCA AGCCACCACG CTCGACCGGG GGACGGCGAA TCCCCGGGAA   1560

TTGAAATAAA TTGCAATTCA GGTCAATGCG GCCAGCGATT GGACACATCT CCAAGGCACA   1620

GGGCCATTCT GCAGTGCCGG GGATTCAGTG CATTCCCCG GGCCGGGCCC GACACGCGAT    1680

AGGCTGGTTC TTCCACACCA CCGGAGATTC GTCGTTCTGA AGAGCTGAAG TGGCGAGATG   1740

GTCTCTGCAG GAATTCAAGC TAGATGCTAA GCGATATTGC ATGGCAATAT GTGTTGATGC   1800

ATGTGCTTCT TCCTTCAGCT TCCCCTCGTG CAGATGAAGG TTTGGCTATA AATTGAAGTG   1860

GTTGGTCGGG GGTTCCGTGA GGGGCTGAAG TGCTTCCTCC CTTTTAGACG CAACTGAGAG   1920

CCTGAGCTTC ATCCCCAGCA TCATTAGATC TCAGCAATGC GTCATTTCTG GCTTTTGCCA   1980

GCTGTTGCTG GTATCGCTGG GGCTCAATGC CCCTACCTGT CGGGTGAAAT GAGTTTCACC   2040

CAGGAGCAGG ACAATGCTGG CGATACCATT GAGGTCACGG AGCAGCCCAT TGACAACACC   2100

CTGTATGTCA ATGACACCGG TAGCTACATG ACTACCGACT TTGGCACTCC GATCTCCGAC   2160

CAGACCAGTC TCAAGGCCGG GCCCCGTGGT CCTACCCTGT TGGAGGACTT TATCTTCCGT   2220

CAGAAGCTTC AGCGGTTCGA CCATGAGCGT GTAAGTACAG TAACTGCTGC GGTGTGTAGT   2280

AACAATAAAT TGACCCAGTG GTTTTCAATT AGGTCCCCGA GCGCGTCGTC CACGCCGTG    2340

GTGCCGGTGC ATATGGTACT TTCAAATCCT ACGCCGACTG GTCGAACGTC ACGGCTGCCG   2400

ATTTCTTGAG TGCCAACGAT AAGGAGACCC CTATGTTCTG TCGCTTCTCT ACTGTGGTCG   2460

GTTTCCGTGG TAGTGTTGAC ACTGCGCGTG ATGTTCACGG TCACGCTTGT CGGTTCTACA   2520

CTGACGAGGG TAACTATGGT ATCTTGATAT GGTCACCCAA CAATAATTCA ATACATGCTA   2580

ACAGATATGT CTCTACTAGA CATCGTCGGT ATCAATTTCG CCCCCTTCTT CATCCAGGAC   2640

GCCATCCAGT TCCCCGATCT TGTCCACGCC ATCAAGCCCA TGCCCAACAA TGAGATCCCC   2700

CAGGCCGCTA CTGCACACAC TTCCGCTTGG GACTTCTTCA GCCAGCAGAG CACTGCCCTC   2760

CACAGTGCCT TGTGGCTGAT GTCTGGTAAC GGTATTCCTC GTTCTTTCCG CCACATGAAC   2820

GGCTACGGAG TCCACAGCTT CCGCTTCGTC GCTGCCAATG GCACTTCCAA GGTGGTGCGA   2880

ACACCTTGGA AGTCCCAACA GGGTGTTGCC AGTCTGGTGT GGGATGAAGC TCAGGCCGCT   2940

GCTGGTAAGA ACAGTGACTA CCACCGCCAG GATCTGTACA ATGCGATGCC CAATGGCCAC   3000

TACCCGAAAT ACGAGGTCAG CCAATCCCTT GATGTCTATC GATAGAGCCT TTGCTGACA   3060

ATCCCCTAGC TCCAAGCCCA GATCATGGAT GAGGCTGACA TGCTTCGTTT CGGCTTCGAC   3120

CTTCTGGATC CCACCAAGTT GGTCCCCGAG GAGGTTGTCC CTTACACTCC TCTCGGAATG   3180

ATGGAGCTCA ATGCCAACCC CACCAACTAC TTTGCTGAAG TTGAACAGGC TGGTGTATGT   3240

ATTCCCCATT CATCAAATGC CAGACATAAT CTAACTTCTG CAGTTCCAAC CCGGTCACGT   3300

CGTTCCTGGC ATTGACTTCA CCGACGACCC CCTGCTGCAA GGCCGTCTCT TCTCCTACCT   3360

CGACACTCAG TTGACCCGTC ACGGCGGTCC CAACTTCGAG CAAATCCCCG TCAACCGTCC   3420

TCGCAAGCCC GTTCACAACA ACAACCGTGA CGGCTTCGGC CAGCAGCAGA TCCCCACCAA   3480
```

| | | | | | | |
|---|---|---|---|---|---|---|
| CAACTGGGCC | TACACCCCCA | ACAGCATGAG | CAACGGTTAC | CCCATGCAAG | CCAACCAGAC | 3540 |
| CCAGGGTCAT | GGTTTCTTCA | CCGCGCCCTA | CCGCTACGCT | TCCGGCCATC | TCGTCCGCCA | 3600 |
| GACCAGCCCG | ACCTTCAATG | ACCACTGGTC | CCAGCCCGCC | ATGTTCTGGA | ACTCTCTGAT | 3660 |
| CCCCGCTGAG | CAGCAGATGG | TTGTCAACGC | CATTGTCTTT | GAGAACTCCA | AGGTTAACAG | 3720 |
| CCCCCACGTT | CGGAAGAACG | TTGTCAACCA | GCTGAACATG | GTCAACAACA | ACCTCGCCGT | 3780 |
| CCGTGTCGCT | CGTGGTCTTG | GTCTCGATGA | GCCCTCCCCC | AACCCGACTT | ACTACACCTC | 3840 |
| CAACAAGACC | TCCAACGTCG | GTACCTTCGG | CAAGCCCCTC | CTCAGCATCG | AGGGTCTGCA | 3900 |
| GGTCGGCTTC | CTGGCCTCGA | ACTCCCACCC | CGAATCCATC | AAGCAGGGCC | AGGCCATGGC | 3960 |
| CGCGCAGTTC | TCTGCCGCTG | GCGTCGACCT | GAACATTGTC | ACCGAGGCCT | ACGCCGATGG | 4020 |
| TGTCAACACC | ACCTACGCCC | TGTCTGATGC | CATCGACTTT | GACGCCCTCA | TCATCGCCGA | 4080 |
| TGGTGTGCAG | AGCCTCTTCG | CCTCCCCCGC | TCTCGCTAAC | CAGATGAACT | CTACCGCCAC | 4140 |
| CTCTACTCTC | TACCCTCCTG | CCAGACCTTT | CCAGATCCTG | GTCGATTCTT | TCAGGTACGG | 4200 |
| TAAGCCCGTG | GCTGCTGTCG | GCAGTGGCAG | TGTTGCGCTC | AAGAACGCTG | GTATTGATTC | 4260 |
| CTCCCGCTCT | GGTGTGTACA | CTGGCTCGAG | CGAGACGACG | GAGAAGATCG | CCAAGGAGGT | 4320 |
| CTTGGAGGGA | CTCTACACTT | TCCGTTTTGT | GGACCGGTTT | GCGCTGGATG | AGTAAGGGTA | 4380 |
| TCACGTTTGT | ACTTGTACTC | ACGTTCATCG | TTTGTGATGA | TACATTGATT | GATCGATAGT | 4440 |
| CTAGAGTCGA | CCGCGACGGT | GACCGACACC | TGGCGGTAGA | CTATTTATTC | CTGTTGATAT | 4500 |
| GAAGGATGAG | CATGAGGGTA | ATTGCTCATA | TAATCATGTA | TGTAGTGGAT | GTGCATAAGA | 4560 |
| GCAACGAAAT | GGAAGCCTGA | TCATGTGATT | GTATTGCGAC | CGACGGAAAT | TGAGGATATG | 4620 |
| CGGAGATACG | GACAGTGCCA | GAGCCATTGT | CTTCACGTAA | AGTACCAGAC | GGTCCTGAT | 4680 |
| TTCTTCTTGC | ACATAGCATT | AGGCAATTGA | CATGTTGTCG | CTCTACTGAT | ATCACTGTCC | 4740 |
| CTCAAAGCAT | AGCCATGAGC | TCATCTTAGA | TCCAAGCACG | TAATTCCATA | GCCGAGGTCC | 4800 |
| ACAGTGGAGC | AACAGCAGCA | TCCATCATTG | CTTCTCCCCC | AGGGGCCTCT | TAGCGACTAA | 4860 |
| ACCTGGAGTA | TGTCTCAACC | AGCCAATGAA | TCGTCTTCGC | TTCAATGTCC | TTGACACTTC | 4920 |
| TGAGAGGGTC | CCCATCCCTC | AATGCTAATT | CAAAATATAG | CCGAGATGCA | TGGTGGAGTC | 4980 |
| CAAAGTAGAC | AGTATTGCCG | GAATGACGGG | GCCAGTTGCG | CCGAGGTCAT | TGGCCGGCTG | 5040 |
| TGATGCCATC | TGCCACTAAA | TCCGATCATT | GATCCACCGC | CCACGAGGGC | CGTCTTTGCT | 5100 |
| TTTGCGCTGC | GTCCAGGTTC | ACACATCTCT | CTCTCTGCAG | CTCCAGACTG | ACCAGACTAT | 5160 |
| TCTACTTACT | GGTCTGATCG | GCTCCATCAG | AGCTATGGCG | TTATCCCGTG | CCGTTGCTGC | 5220 |
| GCCATCGCTA | TCTTGATCGC | GAGCTCGAAC | TCACTTCTTG | TTTTAATAGT | TGTTCTCGGT | 5280 |
| GACTGAGTGT | CGGTGAGTGA | CAGACCACAA | CACCATTGTT | GCAGGGGTA | AATTTATTCA | 5340 |
| ATTCAGGAAT | TGGATTGTTC | GTCCCGCCAT | GATGTTCTTG | CCGGCTTTGT | TGGCCCTGTT | 5400 |
| TGTCGGATGC | GACGCCCTCG | CTGTGCAGCA | GGCAGGTACT | GCTGGATGAT | GAGCCGTCGG | 5460 |
| TCTCCGCGCG | CAAGCCTAAC | TTCCTCTTCA | TTCTTACGGA | TGATCAGGAT | CTGCAGATCG | 5520 |
| AATTCCACCG | GCGTATATGC | CGTATACACA | GGCGAGAATC | AAGGAGAAGG | GTACTGAGTT | 5580 |
| TTGAATCATT | TGTTACTACT | GGCTCTGTGC | TGTCCGTCGC | GCGTGAGTCT | TTGGACGGAA | 5640 |
| GACAGGCTCA | TAATACTAAT | GTGACGGATG | TGAACCCGCC | TTATGGTATG | AATACCTCTC | 5700 |
| AGATCGGTCA | TGTTTCTTCG | GTGTAAAATT | GCTAATGCAG | CATAGGCGGA | TACCCCAAGT | 5760 |
| TCGTCGCCCA | AGGCTTCAAC | GAAAACTTCC | TCCCCGTTTG | GCTGCAGTCC | GCCGGTTACA | 5820 |
| ATACCTTCTA | CACGGGGAAA | CTGTTCAACT | GCCACAGCGT | CGCTACCTAT | AATGCACCGT | 5880 |
| TTGTGAACGG | CTTCAATGGC | TCTGATTTCC | TCCTCGATCC | CCACACCTAT | TCCTACTGGA | 5940 |

```
ACGCGACGTA CCAACGAAAC CATGAGCCTC CGCGGAGCTA CGAGGGACAA TACACAACGG    6000
ATGTGATGCG GGAGAAGGCA TCGGGGTTGT TGGCAGATGC GCTGGACAGG ACGCGCCGTT    6060
CTTCTGACGG TGCCTATCCG CCGCACACGA ACATCGATAA GCTTATCACC GTCCCTTATC    6120
AGCCACCCGT CGCCATTTGC TCTACGCAAG AGTTACAGGA CTAAGTACTT CGCAGCCTGC    6180
TTATCTGCAT CAAATCGTCG TACCGCATTA ATCCGTGCC ACCCTATAAT AGCCTGCAGG     6240
ATCAATACCG TTTTGACATC CGATGCCGCA GTCTGACTAC CCGTGCTCGA CATTAGTTTG    6300
TATGCGTATC GTAGCGGCAA GTTGCATTTC TATATCATTC ATAACCATCA AAACTTTTTT    6360
CCTCATTTTA TAGTATTAGT TTCCGCCGAC ACGGGCCAGG TACGCCTCCC AACCTTCCTT    6420
CTGGTACTGT TGCGCAGCCT GCACCGGGTC CGGCGCGGCG TAGATACCGC GACCCGCGAT    6480
AATGAAGTCA GCACCCCGAC CGATAGCCGA TGCGGGAGTC TGGTACTGCT GACCGAGCTT    6540
ATCTCCCTTG GACGAAATGT TCACACCAGT CGTGAAGACC ACAAAGTCCT CCTCATCCGA    6600
AGGAGAGCTG ACTTCCGACT GCACCTCACC CAACGAGCGG GTCGACACAA ATCCCATGAC    6660
GAAGTTCTTG TATTTCCGGG CATAATCAAC CGAAGAAGTA GTGTACTGGC CGGTGGCCAA    6720
GGAACCCTTA GAGGTCATTT CCGCCAAGAT CAACAGACCA CGTTCGGGGC CGTAGGAGAA    6780
GTCCGGTGCA GACGCCGTCT GAGCGAGAGC CTCGACGATA CCCTCGCCAG GCAGGATGCT    6840
GCAGTTGATG ATATGGGCCC ATTCTGAGAT GCGGAGGGTA CCACGGTGGT ATTGCTTCTG    6900
GACAGTGTTG CCAATGTCGA TGAATTTGCG GTCCTCGAAG ATGAGGAAGT TGTGCTTCTG    6960
CGCAAGAGCC TTGAGGCCCT CAATGGTCTC GTCGCTGAAG TCAGAGAGGA TATCGATGTG    7020
GGTTTTGATC ACGGCGATGT AGGGACCGAG ACCTCAGTCC GGTATCACCG TTAATAAGTT    7080
TGTATGCAGC ATAAACAGGC AGAATGGCGG GTCGGCCTAC GGTCAGCAAG ATCTAGTAGC    7140
TCCTTAGTGG TGGTAACGTC GGCAGAGACG GTCACATTGG TCTTCTTGGC CTCAGCAATT    7200
TCGAACAGCC GCTTGGCCAG AGCATTGGGG TGCTTGCTGG CACGGGCAGT GTAGGTCAAT    7260
TGCGACTTGG AGGACATGGT GTCGGTGGAG GGGTTAATGC GGGGATGAAA GAGGCTTGTG    7320
CAATATGAGT AGCTTGGAGT TTCGACTGAT AGGCCCTAAT TGGTAGATCC AGAGATGCGC    7380
AAATACTACC GAATAATTTA GCAGCGACTG GCCCTTATAT GAGGTGAACA ATGCACATTC    7440
AATGTCGAGC AAAAGAGGAG CTCAGTAAAT CATCGCGACC CTCCACGCAC CAGCCACATC    7500
GGGTGATTTC GCCGCCTCCG ACCGGAACCG TGGGGTTCAG CCACACCTGC AAAGGCAGTT    7560
CCTTTCCATT GAAGTTGCCA CACCCAGGTT CATTGGAGCT CGTATTTTTC CCTGCTGCAC    7620
ATGGGGAAAT AGACCAGCTC AATCAGAAAG CCATTGTCAT TCCCGACCCT AGCAGTACGC    7680
ATAGTAAACG CGTCGTGGAG TAGTAATATA CAAGTGAGAA ATTTATTACA TATAGCGTGG    7740
TATAGCCAAC AGCGCCAATC ACACCCGACG GAAGTCAATC CAAACTTTAA AAGGTAGGGA    7800
AATCAACTCC CTCGCGACTT CCAAAAGAGG TCAATCCCCA AAGAGCTCCC TGTGCAAGCA    7860
AGTAGAAGCT GCCGTACAAC CGGACCGACC CCGGCTTGCC GGAGTACACG TATCCGTAAA    7920
GGAACAGTGA GCGACCGAGA ACCCAAATGC TTCCAAGGCC AGTTGCCAAC TGGGGGTACT    7980
TCAATCCAGC CACCAGGATG AAGAGCATAG TTTGGCTGGA GTTCTCAAGG AAGTTGGCAT    8040
GAGCGTGAGC GAGTTAACTG CTCAGCCTTG GGCTGCACGA TTGGAATGTA TGTTAGCTCG    8100
AGGAATCTTG TCCGTCTGAG GTTGGTAGGT TGGCTTACGT TGTCTTGCAC TGCACTACGG    8160
TCGCATAGCA GTGAGGGTAG GGGCAATCGG CGTTCTTACG GAGACGAGAC ACGACGGCGC    8220
CATGGACGAA GCTCAGGACG GGGATGGCGC CCAGAGCGAC GGCAATGACA GAGCTGCAGG    8280
ATGATTAGCA TCAGACTATA TGGGACCTAA TGGCATTGTT TGCAGGGATT GTGGAATTGG    8340
CACATACCCG TAGTTTTCAG GGACGGTCAG AGTAAGCATG GTGAGATATT AACTTGTAGT    8400
```

```
GTTTTCAATT  TGAATCTGCT  ATGACTAGGC  GGTATTGGGA  AGTCTAGAAG  AAGCCGAAAG      8460

TGATTCAATT  TATATAATCG  GCGATTGATG  GGGCGCAAGA  GCGCGATGCG  GATCCGGCCA      8520

AAACCGTTTA  AAC                                                             8533
```

( 2 ) INFORMATION FOR SEQ ID NO:7:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
ATGTTCTGGA  ACAGCCTGAT  CCCCGCCGAG  CAGCAGATG                                 39
```

( 2 ) INFORMATION FOR SEQ ID NO:8:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
ATGTTCTGGA  ACTCCCTGAT  CCCCGCCGAG  CAGCAGATG                                 39
```

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
ATGTTCTGGA  ACAGCTTGAT  CCCCGCCGAG  CAGCAGATG                                 39
```

PRODUCTION OF ASPERGILLUS NIGER CATALASE-R

FIELD OF THE INVENTION

The invention relates to the application of genetic engineering techniques to create novel strains of *A. niger* which produce high levels of an endogenous catalase enzyme (catR gene product, catalase-R) while generating minimal sodium gluconate waste material. Specifically, high levels of catalase-R are generated through replacement of the endogenous catR gene promoter with the *A. niger* glucoamylase (glaA) gene promoter which results in not only higher levels of catalase-R, but also eliminates the requirement for hydrogen peroxide to act as an inducer for catalase synthesis, and deletion of the endogenous glucose oxidase (goxA) gene greatly reduces the level of sodium gluconate waste product, thereby minimizing the need for expensive waste handling.

BACKGROUND OF THE INVENTION

Catalases [hydrogen peroxide: hydrogen peroxide oxidoreductases (EC 1.11.1.6)] are enzymes which catalyze the conversion of hydrogen peroxide ($H_2O_2$) to oxygen ($O_2$) and water ($H_2O$) according to the following formula:

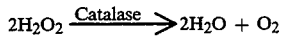

$$2H_2O_2 \xrightarrow{\text{Catalase}} 2H_2O + O_2$$

These ubiquitous enzymes have been purified from a variety of animal tissues, plants and microorganisms (Chance and Maehly 1955 Methods Enzymol. 2: 764–791; Jones and Wilson 1978 in H. Sigel (ed.), *Metal Ions in Biological Systems*, Vol. 7, Marcel Dekker Inc., New York).

Nearly all forms of the enzyme which have been characterized consist of four polypeptide subunits, each having a molecular weight of 50,000 to 60,000 and containing one protohemin prosthetic group per subunit (Wasserman and Hultin 1981 Arch. Biochem. Biophys. 212: 385–392; Hartig and Ruis 1986 Eur. J. Biochem. 160: 487–490). Bovine liver catalase has been the most extensively studied variety of this enzyme [Schonbaum and Chance 1976 in *The Enzymes* (P. D. Boyer, ed.) 3rd edn., vol. 13, pp. 363–408, Academic Press, New York]. The complete amino acid sequence and three dimensional structure of bovine liver catalase are known (Schroeder, et al., 1982 Arch. Biochem. Biophys. 214: 397–412; Murthy, et al., 1981 J. Mol. Biol. 152: 465–499).

Although less well-studied from a biochemical and biophysical standpoint, catalases from filamentous fungi have several characteristics that distinguish them from their mammalian counterparts. While similar in subunit number and heme content, fungal catalases are substantially larger molecules than those from other organisms, having subunit molecular weights ranging from 80,000 to 97,000 (Vainshtein, et al., 1986 J. Mol. Biol. 188: 63–72; Jacob and Orme-Johnson 1979 Biochem. 18: 2967–2975; Jones, et al., 1987 Biochim. Biophys. Acta 913: 395–398). More importantly, catalases from fungi such as *Aspergillus niger* are more stable than beef liver catalase to proteolysis and to inactivation by glutaraldehyde, SDS, and have lower affinity for catalase inhibitors such as cyanide, azide and fluoride (Wasserman and Hultin 1981 Arch. Biochem. Biophys. 212: 385–392). In addition, *A. niger* catalase is significantly more stable than beef liver catalase when subjected to extremes of pH, hydrogen peroxide, and temperature (Scott and Hammer 1960 Enzymologia 22: 229–237). Although fungal catalases offer stability advantages, the corresponding mammalian enzymes such as beef liver catalase appear to have higher catalytic activity (Gruft, et al., 1978; Kikuchi-Torii, et al., 1982). However, since enzyme stability is an important factor in the biotechnological utilization of enzymes, there has been considerable interest in the use of fungal catalases, especially for applications involving neutralization of high concentrations of hydrogen peroxide. Vasudevan and Weiland (1990 Biotechnol. Bioeng. 36: 783–789) observed that the rate of deactivation in $H_2O_2$ was at least an order of magnatude lower for *A. niger* catalase than for beef liver catalase. The differences in stability of these two enzymes can probably be attributed to differences in structural characteristics and composition of the proteins [Vasudevan and Weiland 1990 Biotechnol. Bioeng. 36: 783–789].

Catalase preparations from *A. niger* are sold commercially for diagnostic enzyme kits, for the enzymatic production of sodium gluconate from glucose, for the neutralization of $H_2O_2$ waste, and for the removal of $H_2O_2$ and/or generation of $O_2$ in foods and beverages. Traditionally, beef liver catalase has been the preferred enzyme for diagnostic purposes and for pharmaceutical-related applications (e.g., contact-lens cleaning/disinfection/$H_2O_2$ neutralization). However, recent outbreaks of a slow-virus disease known as BSE (bovine spongiform encephalopathy) in European cattle herds and fear that this disease might be spread to man [Dealler and Lacey 1991 Nutr. Health (Bicester) 7: 117–134; Dealler and Lacey 1990 Food Microbiol. 7: 253–280] have aroused interests in finding alternatives to beef liver catalase for most industrial applications. Little information has been published regarding the regulation of catalase synthesis in *A. niger*. However, it has been observed that catalase is produced in response to the generation of $H_2O_2$ during growth of the organism on glucose or fatty acids. For example, during the metabolism of glucose, $H_2O_2$ is formed by oxidation of the sugar to give gluconate. This reaction is catalyzed by the enzyme glucose oxidase:

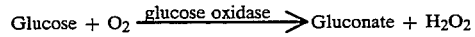

$$\text{Glucose} + O_2 \xrightarrow{\text{glucose oxidase}} \text{Gluconate} + H_2O_2$$

Cellular metabolism of fatty acids, which occurs in specialized organelles known as peroxisomes, also yields $H_2O_2$ which induces the formation of catalase. However, in a distantly related fungus (yeast), *Saccharomyces cervisiae*, a specific catalase is induced during growth on fatty acids. This catalase, termed catalase-A (atypical), is localized chiefly in peroxisomes where fatty acid oxidation occurs. A second *S. cerevisiae* enzyme, catalase-T (typical) is a soluble cytoplasmic enzyme which is synthesized in response to a variety of other metabolic and environmental stresses. These two yeast catalases are the products of two different nuclear genes, designated CTA1 and CTT1. Similarly, two catalase genes have been isolated from *A. niger* (Genencor International, Inc., unpublished). The *A. niger* catA gene, cloned by cross-hybridization to the yeast CTA1 gene, encodes a catalase enzyme which is induced primarily during growth on fatty acids and is presumably peroxisomal. This enzyme (catalase-A) is not of commercial importance at this time, however, a second cloned *A. niger* catalase gene, designated as catR, encodes a soluble cytoplasmic enzyme (catalase-R) which represents the major activity in commercial catalase preparations.

Because of the obvious commercial interest in *A. niger* catalases, it would be desirable to obtain *A. niger* strains which produce increased levels of the catR gene product. Furthermore, it would be a significant advantage to effect high levels of catalase synthesis without the need to generate hydrogen peroxide as an inducer. Concomitant with the generation of hydrogen peroxide is the formation of sodium gluconate which represents a waste disposal problem. Thus, it is also highly desirable to minimize the production of gluconate in large scale fermentations with catalase production strains of *A. niger*. This invention discloses a solution for simultaneously accomplishing all of these objectives.

SUMMARY OF THE INVENTION

It has been discovered that it is possible to increase the expression of catalase-R (catR gene product) without the need to supply hydrogen peroxide as an inducer of catalase synthesis. Simultaneously, it was discovered that elimination of glucose oxidase gene expression (by goxA gene deletion) minimizes the generation of gluconate waste material, thereby circumventing the need for expensive waste treatment processes.

The invention includes a gene encoding *Aspergillus niger* catalase-R (catR gene) to which promoter and terminator elements of the *A. niger* glucoamylase (glaA) gene were functionally attached. Concomitantly, the coding region of the *A. niger* glucose oxidase (goxA) gene was destroyed using a targeted gene replacement strategy. The invention also includes a transformed *A. niger* organism which is capable of expressing high levels of catalase-R without hydrogen peroxide induction. This organism contains a functional expression unit comprising the catR gene, to which the *A. niger* glaA gene promoter and terminator sequences have been functionally attached.

The inventors also disclose a method for producing high levels of catalase-R comprising growth of transformed *A. niger* cells which contain chromosomally integrated copies of the catR gene under operational control of the *A. niger* glaA promoter.

FIGURES

FIG. 1 is a diagrammatic representation of the construction of the catR expression plasmid which contains the *A. niger* glaA promoter, catR coding region, glaA terminator and *A. niger* pyrG gene. A linear fragment (EC2L) containing these components was excised by digestion with NotI and PmeI and used to transform the host strain *A. niger* ΔgoxA pyrG metC.

FIG. 2 (SEQ ID NOS: 4 and 5) shows the nucleotide sequence and deduced amino acid sequence of the *A. niger* catR gene and flanking regions. Restriction sites for enzymes recognizing hexanucleotide and octanucleotide sequences are shown. Introns are denoted by dashed lines. Deduced amino acid sequences corresponding to peptides sequenced directly from the catalase-R protein are underlined with a solid bar.

FIG. 3 (SEQ ID NO: 7) is the complete nucleotide sequence of the linear fragment (EC2L) used to transform *A. niger* ΔgoxA pyrG metC.

FIG. 4, Panel A is a diagrammatic representation of the construction of the *A. niger* vector for deletion of the glucose oxidase (goxA) gene. A linear fragment comprising the SmaI-ClaI segment was excised and used to transform the host strain *A. niger* pyrG. Panel B is a schematic showing the expected integration event at the goxA locus which results in replacement of the goxA coding region with the *A. niger* pyrG gene.

FIG. 5 is a graph showing catalase production among strains of *A. niger* ΔgoxA pyrG metC transformed with the catR expression cassette (EC2L). The original parent strain, *A. niger* FS-1, and the host strain *A. niger* ΔgoxA pyrG metC are included as controls. Each strain was grown in duplicate and the assay results from each are shown.

DESCRIPTION OF THE PREFERRED EMBODIMENTS

The details of the catR expression vector construction and genetic modifications used to derive improved catalase production strains are described. One skilled in the art will understand that various changes in the following examples could be made. Accordingly, the examples are not intended to be limiting.

The techniques used in cloning the *A. niger* catR gene and construction of the catR expression cassette are conventional techniques described in Sambrook, et al., 1989 *Molecular Cloning, A Laboratory Manual*, Cold Spring Harbor Press, Cold Spring Harbor, N.Y.

1. Cloning and Characterization of the *A. niger* catR Gene

Purified catalase-R was obtained from a commercial preparation of *A. niger* catalase (Fermcolase 1000, Genencor International, Inc.) and a series of proteolytic fragments were generated. These peptide fragments were subjected to amino acid sequence analysis. The amino acid sequence information was employed to design synthetic DNA probes for identification of catR-specific cDNA sequences contained within a λgt11 library. Briefly, the peptide fragment Met-Phe-Trp-Asn-Ser-Leu-Ile-Pro-Ala-Glu-Gln-Gln-Met was used to design a pool of three synthetic oligonucleotides having the following sequences:

5' ATG TTC TGG AAC AGC CTG ATC CCC GCC GAG CAG CAG ATG 3' (SEQ ID NO: 7)
5' ATG TTC TGG AAC TCC CTG ATC CCC GCC GAG CAG CAG ATG 3' (SEQ ID NO: 8)
5' ATG TTC TGG AAC AGC TTG ATC CCC GCC GAG CAG CAG ATG 3' (SEQ ID NO: 9)

Figures 1, 4A:
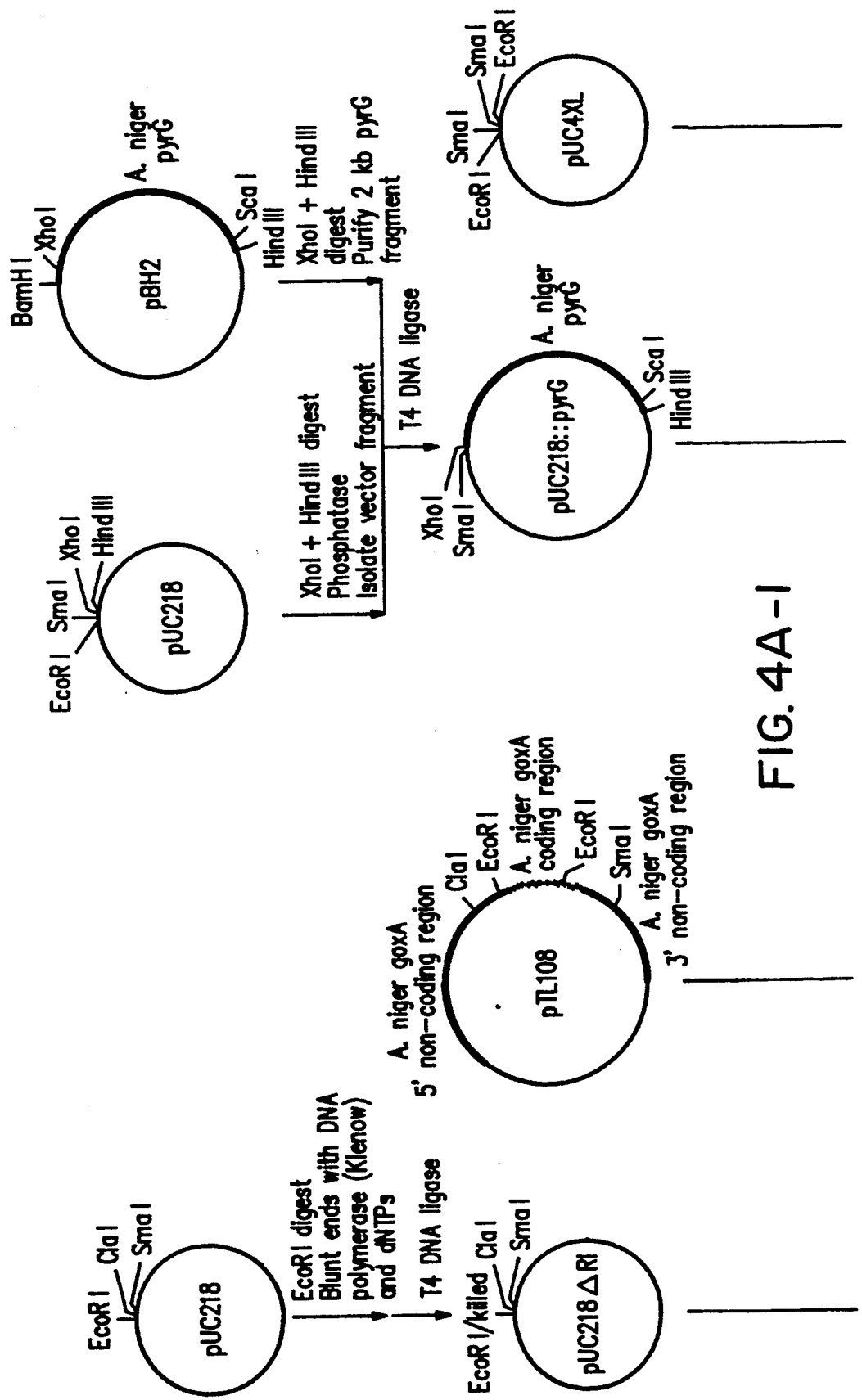
Figures 2, 4A:
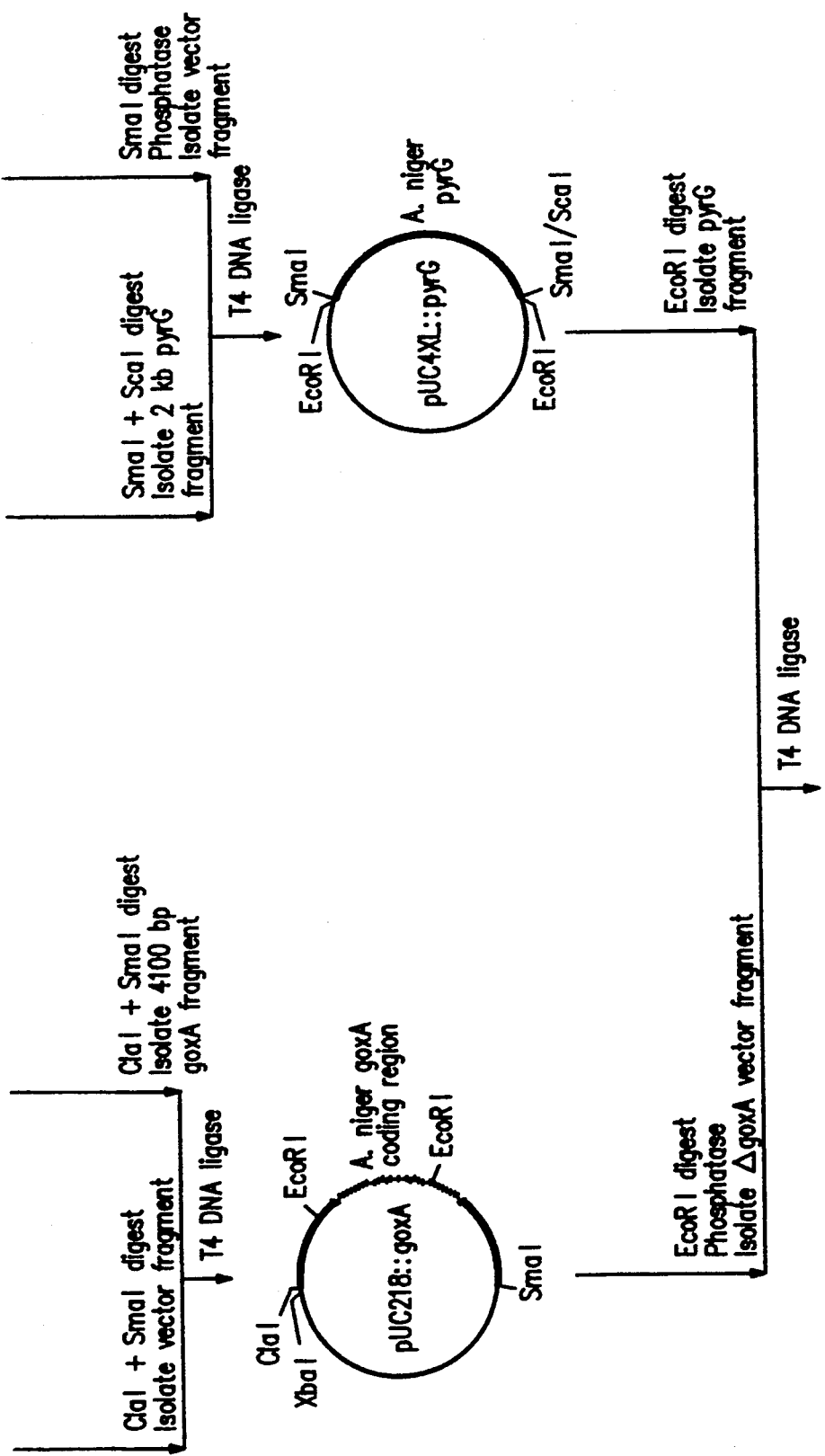
Figures 3, 4A:
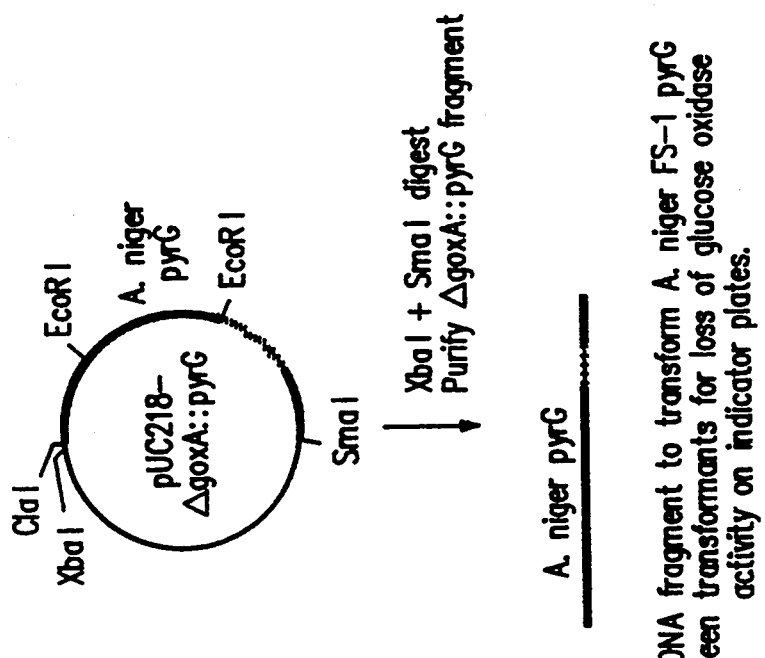
Figure 4B:
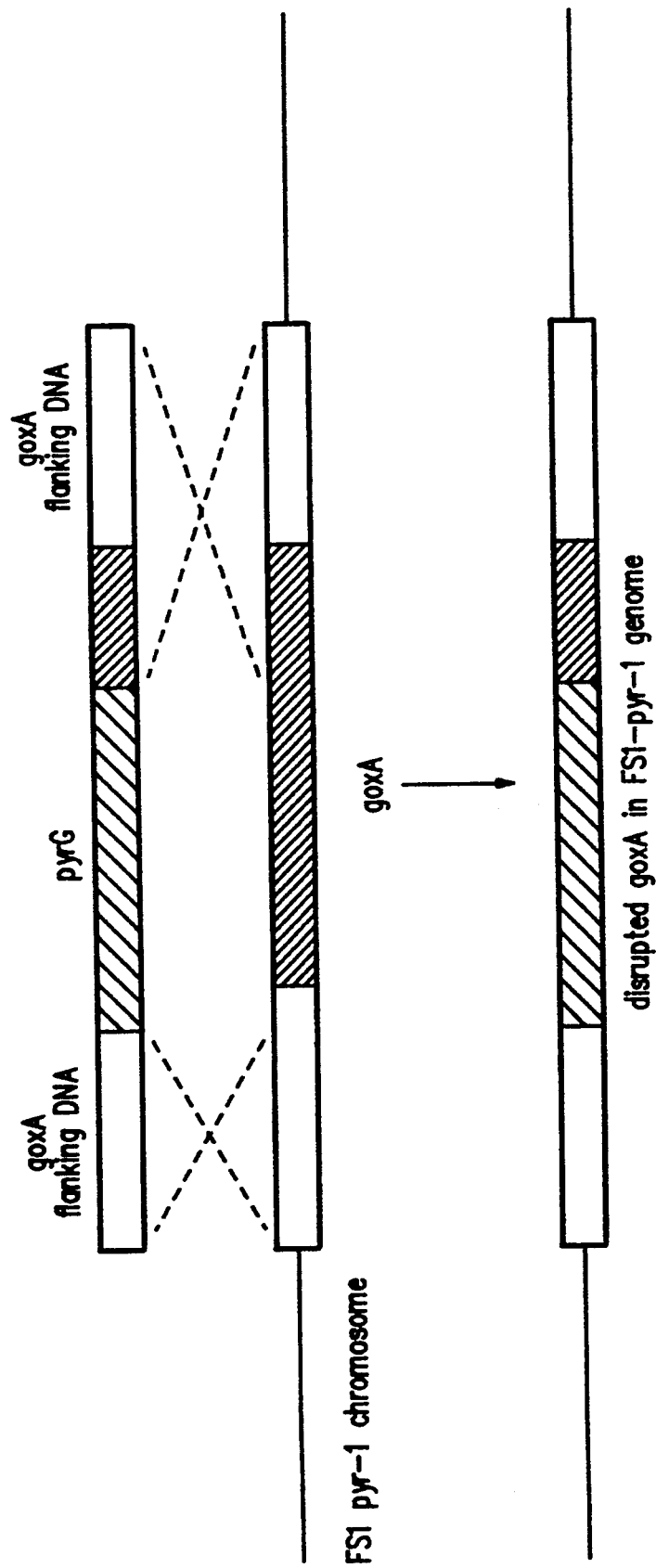

This peptide was chosen because the amino acids give minimally degenerate codon choices, i.e., the differences among the three synthetic oligonucleotides represent alternate codon choices where there was no strong bias in the known codon usage pattern for *A. niger*. This position of this proteolytic fragment corresponds to peptide 3 shown in FIG. 2 (amino acid nos. 487–499 of SEQ ID NOS: 4 and 5). A clone containing a partial cDNA fragment was positively identified by hybridization with the synthetic DNA probe and nucleotide sequence analysis of this clone confirmed that it encoded catalase-R. This cloned cDNA segment was used to probe a library of *A. niger* genomic DNA. Subsequently, the entire catR gene, plus upstream and downstream transcriptional control elements, was assembled as a 9.0 kb HindIII-XhoI restriction fragment. The nucleotide sequence of the catR coding region has been determined and is given in FIG. 3 (SEQ ID NO: 6).

2. Construction of a Catalase Expression Vector-Cassette (EC2) Used for Transformation of *A. niger*

Figure 1B:
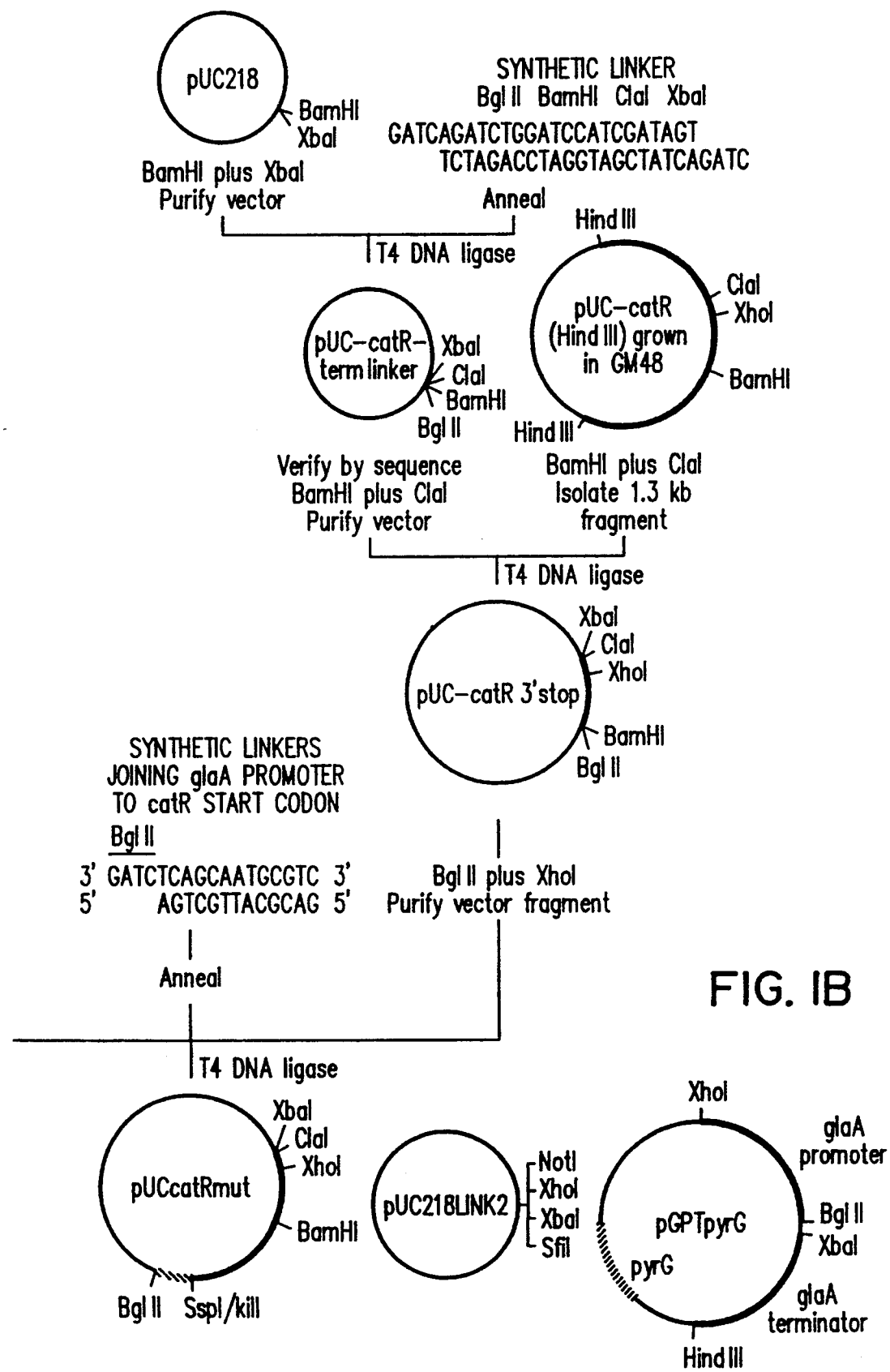
Figures 1, 1C:
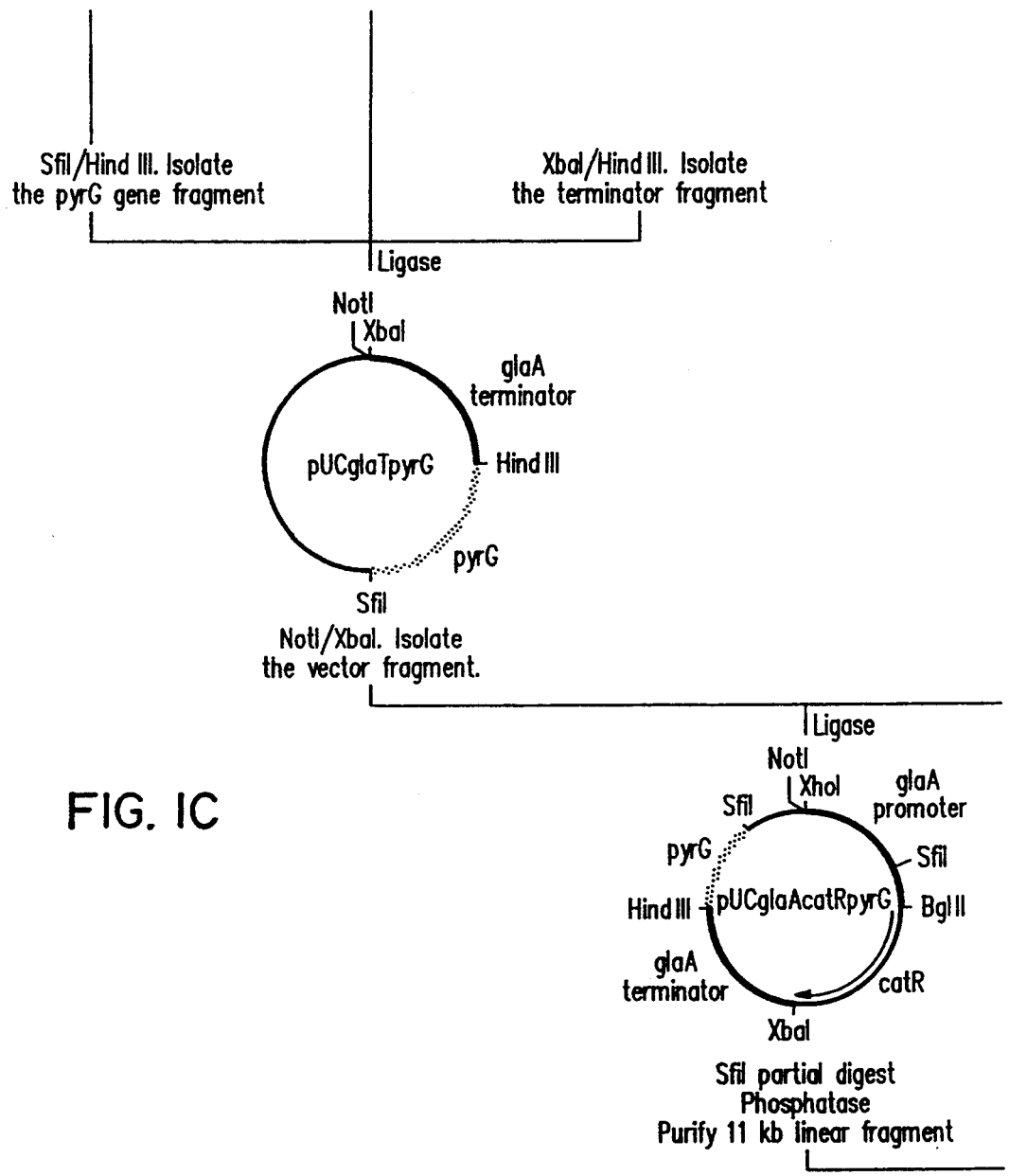
Figure 3F:
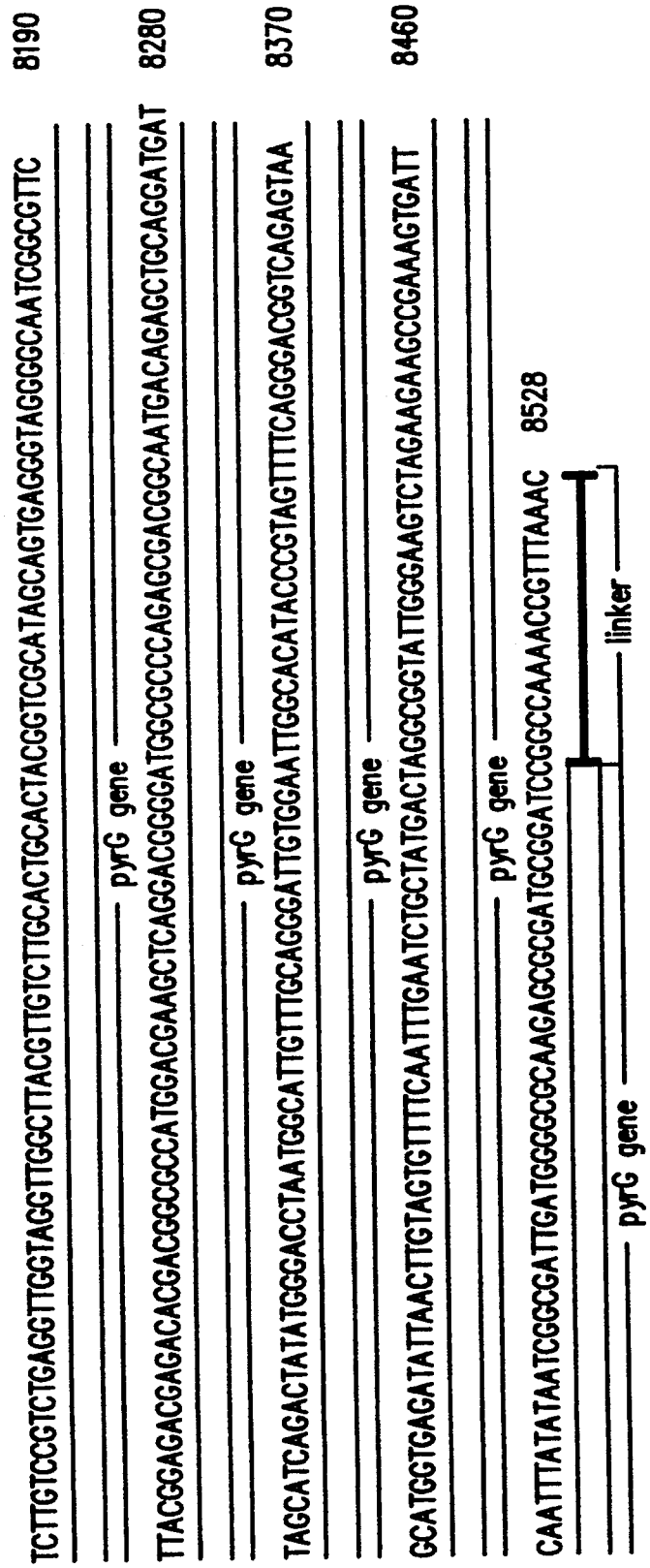

The catR expression vector used for these studies utilizes transcriptional and translational control signals from the well-characterized *A. niger* glucoamylase (glaA) gene. Unlike the catR promoter, the strong glaA promoter does not require $H_2O_2$ for induction. Instead, the glaA promoter responds to the presence of starch, maltose or other malto-oligosaccharides (Nunberg, et al., 1984 Mol. Cell. Biol. 4: 2306–2316; Barton, et al., 1972 J. Bacteriol. 111: 771–777; Fowler, et al., 1990 Curr. Genet. 18: 537–545). Thus, use of the glaA promoter allows construction of catalase production strains which are not dependent on the generation of hydrogen peroxide for induction of catalase synthesis. Construction of the vector-cassette for expression of catalase under transcriptional control of the glaA promoter is outlined in FIG. 1. The essential feature of this construct is that the glucoamylase-catalase expression unit (i.e., glaA promoter+catR coding region+glaA terminator) and the adjacent selectable marker (the *A. niger* pyrG gene) can be excised on a single NotI-PmeI restriction fragment (FIG. 1).

The catR coding region was joined to the glaA promoter utilizing a synthetic oligonucleotide linker (13 base pairs) designed to couple these two DNA segments via a BglII site in the glaA promoter to a unique SspI site four base pairs after the catR start codon (introduced by site-directed mutagenesis). Insertion of this linker restores the nucleotide sequence of catR to that which existed prior to the site-directed mutagenesis and precisely fuses the catR coding region to the glaA promoter. In a description of the glaA promoter region given by Fowler, et al., (1990 Curr. Genet. 18: 537–545) it was noted that there are DNA sequences far upstream of the start codon which are required for high level expression. These sequences, which presumably represent transcriptional enhancer elements, are included on the 1.9 kb glaA promoter segment included in construction of the catR expression cassette. Similarly, the glaA terminator region was linked to the 3'-end of catR via a naturally-occurring ClaI site downstream of the catalase-R gene stop codon. An XbaI site adjacent to ClaI was incorporated using a synthetic DNA linker and was then used to complete the terminator fusion. This terminator segment, which encodes information necessary for proper polyadenylation and termination of transcription, is the same segment as that which was used for Genencor's chymosin expression vector (Cullen, et al., 1987 Bio/Technol. 5: 369–376). A restriction fragment containing the *A. niger* pyrG gene (Wilson, et al., 1988 Nucl. Acids Res. 16: 2339) was subcloned adjacent to the glaA terminator such that the entire glucoamylase-catalase-selectable marker cassette was encoded on a single restriction fragment (the nucleotide sequence of this fragment (EC2L) is given in FIG. 3 (SEQ. ID NO: 6)).

3. Development of *A. niger* Strains to be Used in the Production of Catalase Features of the *A. niger* strain used as a host for expression of the glucoamylase-catalase cassette include a) uridine-requiring auxotrophy, specifically a pyrG auxotrophic mutation, b) deletion of the gene encoding glucose oxidase, goxA, and (c) a methionine-requiring auxotrophy, specifically mutation which renders the cells deficient in cystathionase (metC) activity. While the metC marker is not required for high level expression of catalase-R, it was included as a feature of the host strain to satisfy limited survivability regulation of government regulatory agencies. The catalase expression cassette described above was used to transform the *A. niger* ΔgoxA pyrG metC strain and the resulting transformants were screened in shake flask cultures for their ability to produce high levels of catalase. From these transformants, the highest catalase producers were selected for further study. Shake flask cultures were grown for two days at 33° C. in 50 ml of a liquid medium that was made according to the following recipe: For each liter of medium add maltodextrin [Staley 200, A. E. Staley Co., (100 g)], ammonium sulfate (4 g), calcium chloride (0.4 g), magnesium sulfate (0.6 g), corn steep liquor [Archer Daniels Midland Co., (10 g)], and potassium phosphate (3 g); The volume is brought to 500 ml with distilled water, the pH is adjusted to 7.0, and the solution is autoclaved; Separately a 500 ml solution of 12% calcium carbonate is made in distilled water, the pH is adjusted to 7.0, and the solution autoclaved. The two sterile mixtures were combined aseptically to give one liter of catalase production medium. After two days growth, the mycelia were harvested by filtration (Miracloth, Calbiochem, Inc.), and the cells were rapidly frozen in liquid nitrogen. The cells were disrupted by grinding the frozen pellet in an electric coffee grinder for approximately 60 sec or until a fine powder was obtained. The disrupted cells were resuspended in an extraction buffer that contained 100 mM sodium formate, pH 7, 0.01% sodium dodecylsulfate, and 1 mM each of phenylmethyl sulfonyl fluoride and pepstatin. Insoluble debris was removed by centrifugation at approximately 1500 g, and the activity of soluble catalase in the extract was measured by previously described methods (Patti and Bonet-Maury 1953 Bull Soc. Biol. 35: 1177; Teranishi, et al., 1974 Agric. Biol. Chem. 38: 1213). Specific methods for generation of the catalase production organisms are outlined below. The parental strain for all studies described herein was *A. niger* FS-1 (NRRL3).

Isolation of *A. niger* FS-1 pyrG Strains

5-Fluoro-orotic acid (FOA), a toxic analog of orotic acid, has been used to select uridine-requiring auxotrophs in filamentous fungi and yeasts (VanHartingveldt, et al., 1987 Mol. Gen. Genet. 206: 71–75). Fungal strains deficient in orotidine-5'-monophosphate decarboxylase (pyrG gene product), are resistant to FOA and require exogenous uridine for growth. The *A. niger* pyrG gene was cloned (Wilson, et al., 1988 Nucl. Acids Res. 16: 2339) and used as a selectable marker for the transformation of pyrG mutant strains. An advantage of using FOA as a positive selection for pyrG auxotrophs is that spontaneous mutants can be selected without need for excessive mutagenesis and screening. The method of selecting *A. niger* FS-1 pyrG mutants is as follows: Spores of *A. niger* FS-1 were spread onto the surface of minimal medium plates containing 2 mg/ml uridine and 1.2 mg/ml FOA. Resistant colonies ($FOA^r$) were evident after 2–3 days growth at 37° C. Spores from six $FOA^r$ colonies were streaked onto fresh medium containing FOA, and isolated colonies were picked for further analysis. Three of the six $FOA^r$ strains were shown to require uridine for growth. To determine which of the uridine-requiring strains had a non-functional pyrG gene, each of the strains was tested for its ability to be transformed (i.e., complemented) with a plasmid containing the *A. nidulans* pyrG gene. Only one strain, FS-1 pyrG1, gave transformants (an approximate frequency of 10 transformants per μg DNA) indicating that it carried a pyrG mutation. This strain was used for all subsequent experimentation.

Generation of *A. niger* FS-1 ΔgoxA Strains

To generate a chromosomal deletion in the goxA gene, a vector was constructed which contained 5'- and 3'-flanking DNA sequences from the goxA gene and a selectable pyrG gene inserted in place of a portion of the goxA coding region (see FIG. 4). For complete information regarding the nucleotide sequence of the goxA gene, consult Frederick, et al., 1990 J. Biol. Chem. 265: 3793-3802 989 and Kriechbaum, et al., 1989 FEBS Lett. 255: 63-66. Briefly, a 4.1 kb ClaI-SmaI fragment comprising the *A. niger* FS-1 goxA gene was subcloned into a pUC218-derivative (from which the EcoRI site had previously been removed) to give pUC218goxA. The *A. niger* pyrG gene was isolated from pUC4XL as an EcoRI fragment having 27 bp and 16 bp of pUC4XL polylinker DNA at either end. The goxA coding region was subsequently removed by digestion with EcoRI and the remaining plasmid fragment was ligated with the EcoRI fragment containing the *A. niger* pyrG gene to create pUC218ΔgoxA. From this plasmid a 4.75 kb SmaI-XbaI restriction fragment which contains 5'- and 3'-flanking regions of the goxA gene with part of the goxA coding sequence removed and replaced with a functional pyrG gene was isolated. Use of this fragment to transform *A. niger* FS-1 pyrG1 with selection for uridine prototrophy resulted in the isolation of several strains which failed to give a blue color on glucose oxidase indicator plates (Witteveen, et al., 1990 Appl. Microbiol. Biotechnol. 33: 683-686). Southern blotting analysis of genomic DNA extracted from these goxA-deficient transformants indicated that the ΔgoxA::pyrG cassette had integrated via a homologous recombination event at the goxA locus (as diagramed in FIG. 4B). In other words, the selectable pyrG gene had replaced the goxA coding region.

Figure 5:
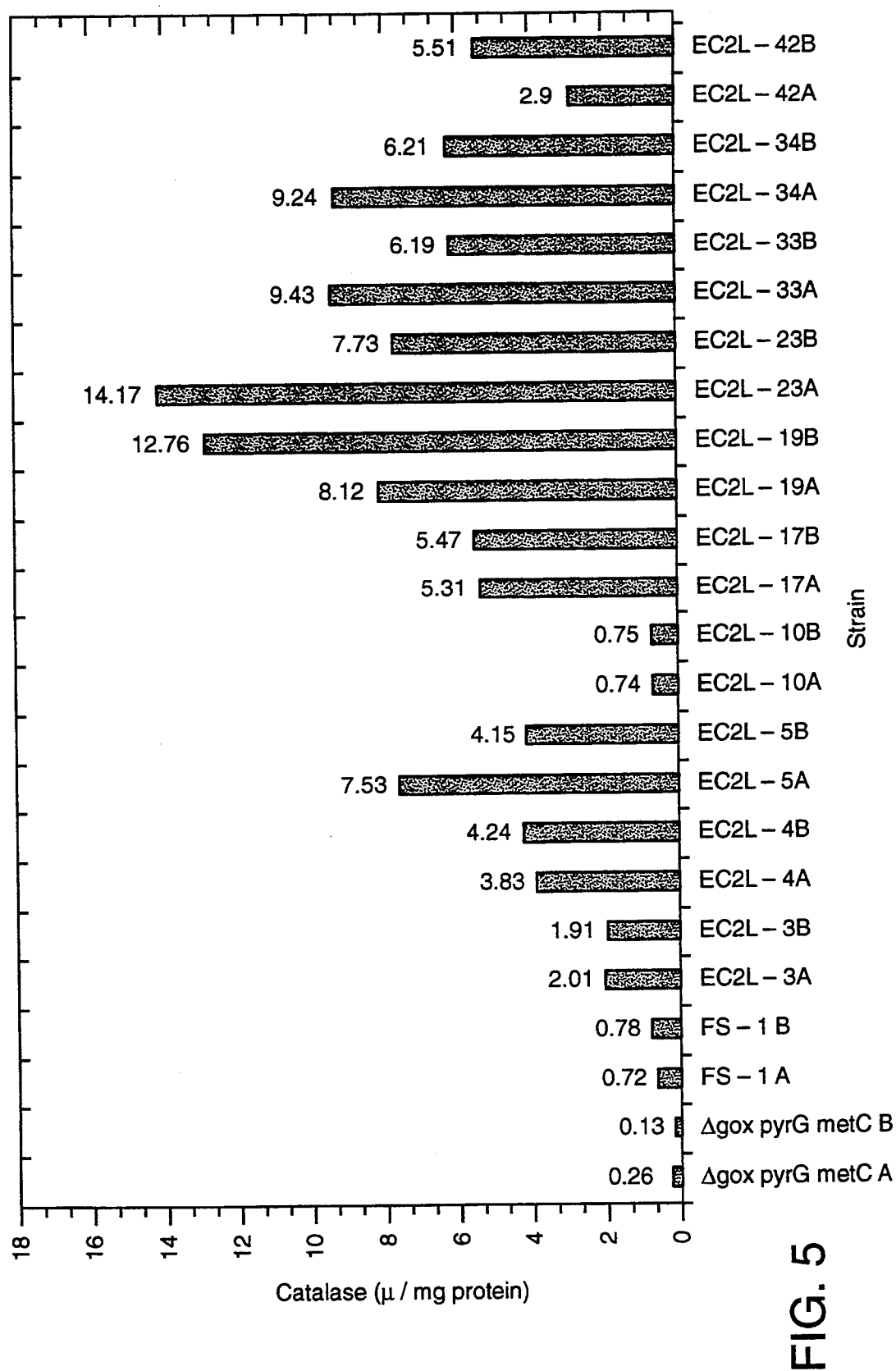

As shown in FIG. 5, catalase production in ΔgoxA mutants was approximately three- to six-fold lower than the parental strain FS-1. We interpret these data to indicate that in the absence of glucose oxidase little hydrogen peroxide is generated, and this in turn has an adverse effect on catalase induction.

Isolation of *A. niger* FS-1 ΔgoxA pyrG Strains

Spontaneous uridine-requiring mutants of *A. niger* FS-1 ΔgoxA were selected using FOA as described above. This step was necessary for subsequent transformation of the strain with the pyrG-based EC2 cassette.

Isolation of an *A. niger* FS-1 ΔgoxA pyrG metC Strain

In order to limit the survivability of a recombinant catalase production organism in the environment, a methionine-requiring auxotrophy was introduced in the following manner. Spores of *A. niger* FS-1 ΔgoxA pyrG were mutagenized with UV light (95% killing) and survivors were subjected to filtration enrichment in Aspergillus minimal medium. With this technique, unwanted prototrophs germinate and grow to form mycelia which can be removed by filtration. Auxotrophic cells cannot germinate or grow in minimal medium, and therefore pass through porous filters (e.g., Miracloth, Calbiochem, Inc.). After several rounds of filtration and growth, the remaining spores were plated onto complete medium. Colonies were patched from these plates onto minimal medium agar and to fresh complete medium plates. Those which grew on complete medium but not on minimal agar were auxotrophic. From the population of auxotrophs, one colony was identified which grew on minimal medium supplemented with methionine. Upon further testing, it was discovered that the strain was defective in a specific step of the methionine biosynthetic pathway. Growth was supported by the addition of either homocysteine or methionine, but not by either homoserine or cystathionine. Based on the known biosynthetic pathway for methionine, it appears that this methionine-requiring auxotroph was deficient in cystathionase activity, and thus, it was given the designation of metC by convention with other organisms.

4. Transformation of the *A. niger* FS-1 ΔgoxA pyrG metC Strain and Characterization of Catalase Overproducing Strains The catalase expression cassette (in linear form) was isolated following digestion of the pUC-EC2 plasmid with PmeI and NotI and purification of the EC2 fragment by preparative gel electrophoresis. The purified DNA fragment was then used to transform the *A. niger* ΔgoxA pyrG metC strain, and prototrophic transformants were screened in shake flask culture for their ability to produce catalase. From approximately fifty transformants screened in shake flasks, ten were identified that produced significantly higher catalase levels than control strains. These ten strains were re-evaluated in duplicate shake flask cultures, and the results of catalase activity assays are shown in FIG. 5. Nine of the ten strains produced significantly higher levels of catalase-R than the parent strain FS-1. Two of the transformants (EC2L-19, EC2L-23) produced catalase yields in shake flask cultures that were roughly ten to fifteen times the level produced by *A. niger* FS-1, and these strains were chosen for testing under large scale production conditions. Fermentation experiments at the 10 liter and 50,000 liter scale have shown that catalase-R production from transformant EC2L-23 corresponds to the level of catalase-R expression seen in shake flask studies.

Furthermore, HPLC analyses of organic acids produced during fermentations of *A. niger* EC2L-23 and the parental strain FS-1 gave the following yields of sodium gluconate:

| Strain | sodium gluconate (mg/L) |
| --- | --- |
| FS-1 | >200,000 |
| EC2L-23 (run 27) | 48 |
| EC2L-23 (run 28) | 123 |

These data show a dramatic decrease in the production of sodium gluconate waste material by transformant EC2L-23.

What is claimed is:

1. A gene sequence encoding catalase R from *Aspergillus niger* in which the *Aspergillus niger* catR gene region consists essentially of the DNA sequences set forth in nucleotides number 1957 through 4370 in SEQ ID:NO 6 and wherein the native *Aspergillus niger* catR promoter has been deleted and an *Aspergillus glucoamylase* promoter gene has been functionally attached and consists essentially of the DNA sequences set forth nucleotides number 1 through 1956 in SEQ:ID NO 6.

2. The gene sequence according to claim 1 wherein the *Aspergillus glucoamylase* promoter is from *A. niger*.

3. The gene sequence according to claims 1 or 2 which has been inserted into a replicable plasmid of a vector capable of integration into an *Aspergillus niger* genome.

4. *Aspergillus niger* which has been transformed with a gene fragment comprising an *Aspergillus niger* catR gene without the *Aspergillus niger* catR promoter and functionally attached to an *Aspergillus glucoamylase* promoter gene wherein said gene fragment consists essentially of the glucoamylase promoter DNA sequence numbered 1 through 1956 in SEQ ID: NO 6 and the *Aspergillus niger* catR coding region DNA sequence numbered 1957 through 4370 in SEQ ID: NO 6.

5. The *Aspergillus niger* according to claim 4 wherein the glucoamylase promoter is from *Aspergillus niger*.

6. The *Aspergillus niger* according to claim 4 wherein the native glucose oxidase gene is deleted.

7. The gene sequence consisting essentially of SEQ ID NO: 6 which has been inserted into a replicable plasmid of a vector capable of integration into an *Aspergillus niger* genome.

8. A replicable plasmid of a vector capable of integration into an *Aspergillus niger* genome which carries the gene fragment consisting essentially of the sequence set forth in SEQ ID NO: 6.

9. A method of overproducing an active gene product of the catR gene which comprises culturing *Aspergillus niger* transformed with the catR gene to which an *Aspergillus niger* glucoamylase promoter is functionally attached using assimilable sources of carbon and nitrogen and wherein the glucose oxidase gene is deleted and the glucose oxidase gene product is absent in said transformed Aspergillus.

\* \* \* \* \*